(12) United States Patent
Fischell et al.

(10) Patent No.: US 6,354,299 B1
(45) Date of Patent: Mar. 12, 2002

(54) IMPLANTABLE DEVICE FOR PATIENT COMMUNICATION

(75) Inventors: David R. Fischell, Fair Haven, NJ (US); Stephen T. Archer, Sunnyvale, CA (US); Robert E. Fischell, Dayton, MD (US); Adrian R. M. Upton, Hamilton (CA)

(73) Assignee: NeuroPace, Inc., Sunnyvale, CA (US)

( * ) Notice: Subject to any disclaimer, the term of this patent is extended or adjusted under 35 U.S.C. 154(b) by 0 days.

(21) Appl. No.: 09/609,086

(22) Filed: Jun. 30, 2000

Related U.S. Application Data

(63) Continuation-in-part of application No. 09/483,806, filed on Jan. 15, 2000, now Pat. No. 6,134,474, which is a continuation of application No. 08/957,869, filed on Oct. 27, 1997, now Pat. No. 6,016,449.

(51) Int. Cl.[7] .............................................. A61B 19/00
(52) U.S. Cl. ..................................................... 128/899
(58) Field of Search ...................... 340/384.1; 128/899, 128/905; 600/25

(56) References Cited

U.S. PATENT DOCUMENTS

| | | | |
|---|---|---|---|
| 2,402,392 A | * 6/1946 | Goldschmidt | ................ 600/25 |
| 3,032,029 A | 5/1962 | Cunningham | |
| 3,209,081 A | * 9/1965 | Ducote et al. | ................ 600/25 |
| 3,634,885 A | 1/1972 | Barkley | |
| 3,850,161 A | 11/1974 | Liss | |
| 3,863,625 A | 2/1975 | Viglione et al. | |
| 3,967,616 A | 7/1976 | Ross | |
| 3,993,046 A | 11/1976 | Fernandez et al. | |
| 4,223,678 A | 9/1980 | Langer et al. | |
| 4,295,474 A | 10/1981 | Fischell et al. | |
| 4,566,464 A | 1/1986 | Piccone et al. | |
| 4,592,359 A | 6/1986 | Galbraith | |
| 4,692,147 A | 9/1987 | Duggan | |
| H1347 H | 8/1994 | Greeninger et al. | |
| 5,447,489 A | * 9/1995 | Issalene et al. | ................ 600/25 |
| 5,755,230 A | 5/1998 | Schmidt et al. | |
| 5,824,021 A | 10/1998 | Rise | |
| 5,891,180 A | 4/1999 | Greeninger et al. | |
| 5,995,868 A | 11/1999 | Dorfmeister et al. | |
| 6,016,449 A | 1/2000 | Fischell et al. | |
| 6,018,682 A | 1/2000 | Rise | |
| 6,044,301 A | 3/2000 | Hartlaub et al. | |
| 6,026,326 A | 5/2000 | Bardy | |
| 6,066,163 A | 5/2000 | John | |
| 6,067,473 A | 5/2000 | Greeninger et al. | |
| 6,070,102 A | 5/2000 | Hartlaub et al. | |
| 6,082,367 A | 7/2000 | Greeninger et al. | |
| 6,083,248 A | 7/2000 | Thompson | |
| 6,128,538 A | 10/2000 | Fischell et al. | |
| 6,134,474 A | 10/2000 | Fischell et al. | |

OTHER PUBLICATIONS

H. Fernandez et al., "New System for a Two–Speed Electroencephalograph with an Auditory Device for Diminishing the Length of Seizures," Aviation, Space, and Environ. Medicine, May 1975, pp. 743–744.

* cited by examiner

Primary Examiner—William E. Kamm

(57) ABSTRACT

An implantable device incorporating an acoustic transducer allows information and alerts to be communicated from the device to a patient. Sounds, including but not limited to buzzes, tones, sequences of tones, combinations of tones, complex sounds, and segments of reproduced or simulated human speech, are transmitted from an intracranially implanted portion of the device via bone conduction to the patient's ears, particularly the inner ears. In the disclosed embodiment, the acoustic transducer is used in cooperation with an implantable closed-loop system for the treatment of certain neurological disorders such as epilepsy, migraine headaches and Parkinson's disease, to warn the patient of an imminent seizure or other episode, to provide information to the patient on the state of the implantable apparatus, and to provide reminders and other information to the patient.

35 Claims, 24 Drawing Sheets

IMPLANTABLE DEVICE FOR PATIENT COMMUNICATION

CROSS-REFERENCE TO RELATED APPLICATIONS

This is a Continuation-In-Part of U.S. application Ser. No. 09/483,806, filed on Jan. 15, 2000, now issued as U.S. Pat. No. 6,134,474, which is in turn a Continuation of U.S. application Ser. No. 08/957,869, filed on Oct. 27, 1997, now issued as U.S. Pat. No. 6,016,449.

FIELD OF THE INVENTION

This invention relates to the field of devices implantable within the head of a human being, and more particularly to intracranially implantable medical devices useful in the treatment of neurological disorders.

BACKGROUND OF THE INVENTION

The current state of the art in treating neurological disorders such as epilepsy or Parkinson's disease involves either drugs or the open-loop electrical stimulation of neurologic tissue. Drug therapy has been shown to have significant short and long-term side effects and is often ineffective. In U.S. Pat. No. 3,850,161, Liss describes a continuous closed-loop feedback system which will always feedback part of the brain EEG signal to separate electrodes so that if a large EEG signal occurs it will be fed back in an attempt to cancel out the original signal. This system does not take advantage of recently developed digital signal processing and microcomputer technology by which feedback signals can be activated only when a neurological event occurs, nor does it provide a practical means to recognize and intervene during early stages in the evolution of a neurological event. In addition, the Liss device is not programmable and it does not provide a means to record EEG signals. Examples of a "neurological event" are the occurrence of an epileptic seizure or the occurrence of a migraine headache. A "neurological event" is defined herein as either the precursor of an event such as an epileptic seizure, or the epileptic seizure itself. This concept of detecting an electrical precursor that is a first type of neurological event that occurs some time before the "real" event (i.e. anomalous brain electrical activity associated with clinical symptoms) is an important aspect of the present invention. It has been shown that both epileptic seizures and Parkinson's tremors have precursors that occur before and can be used to predict the onset of the clinical symptom. It is also very likely that other neurological events such as migraine headaches and depression would have anomalous electrical activity predictive of the onset of clinical symptoms. Methods for the prediction of epileptic seizures have been published by Elger and Lehnertz, 1998 European Journal of Neuroscience, 10, 786–789 "Seizure Prediction by Non-linear Time Series Analysis of Brain Electrical Activity", and Osorio, Frei and Wilkinson, Epilepsia 39 (6):615–627, 1998 "Real-time automated detection and quantitative analysis of seizures and short-term prediction of clinical onset".

Maurer and Sorenson in U.S. Pat. No. 4,019,518 describe a combined internal/external system for electrical stimulation of the body with biphasic pulses but do not describe any means of detecting neurological events. Fischell, in U.S. Pat. No. 4,373,527, describes a programmable medication infusion system but does not anticipate its use in response to a detected neurological event.

More recently, a device has been approved for human use to stimulate the vagus nerve in a continuous fashion with the objective of decreasing the rate of epileptic seizures. Clinical reports on such devices indicate only a modest degree of success in that only 50% of the patients experience a greater than 20% reduction in the rate of epileptic seizures. Another device that has been recently introduced into clinical practice utilizes continuous stimulation of the thalamus for the treatment of involuntary motion disorders such as Parkinson's syndrome.

Neither of these two open-loop devices described above is highly effective for the treatment of a neurological disorder such as epilepsy, and neither anticipates the use of decision making in order to optimize a response to turn off the neurological event nor the recording of EEG signals.

The automatic implantable cardiac defibrillator is an example of a decision making device having data recording capability that has been successfully used in a decision based closed-loop mode for the treatment of ventricular fibrillation. However, the requirements for detection and treatment of ventricular fibrillation are significantly simpler and certainly different from the requirements for a device to detect and treat an impending epileptic seizure. Specifically, an implantable cardiac defibrillator requires only a single signal, namely the heart's ECG, in order to detect a fibrillation event. What is more, only a single pair of electrodes is required for detection of the fibrillation event and that same pair of electrodes can be used to provide an electrical stimulus for electrical defibrillation. A heart defibrillator electrode is adapted to be placed on or in close proximity to the heart and is not suitable for use as a brain electrode.

Coker and Fischell in U.S. Pat. No. 4,581,758 describe sophisticated signal processing techniques using the sum of squared signals from two microphones to identify the direction with respect to a person from whom human speech originates. Although the Coker and Fischell patent teaches several signal processing techniques which may be applied with others to detect neurological events, the Coker and Fischell method is aimed at identifying the location of the speech source, while one of the goals of the present invention is to utilize the known location of the source of EEG signals to help identify an abnormal EEG which signifies an impending neurological event.

The NeuroCybernetic Prosthesis System, recently made available for the treatment of epileptic seizures, utilizes continuous open-loop stimulation of the vagus nerve. This device does not sense the onset of an epileptic seizure, and it utilizes wires that are placed in the neck. Because of the frequent motions of such wires, they will have a tendency to fracture. No existing system utilizes electrodes, electrical wires and a control module that are entirely contained within the patient's scalp and essentially all contained within the patient's cranium. Such systems would not have any repeated bending of connecting wires thereby improving long-term reliability. Furthermore, the NeuroCybernetic Prosthesis System does not use a rechargeable battery, nor does it utilize a separate external device controlled by the patient to activate the implanted system at the start of a neurological event in order to decrease the severity or time duration of the neurological event.

Various cochlear and ossicular implant devices are available that amplify ambient sounds and accordingly stimulate the nerves or bones of the inner or middle ear to provide hearing assistance to individuals with hearing loss. See, e.g., Loizou, P. (1998), "Mimicking the human ear," IEEE Signal Processing Magazine, 15(5), 101–130. Such devices are directed to receiving, amplifying and transmitting sounds present in the external environment; they do not provide any therapy or additional information (not derived from environmental sound) to their users.

SUMMARY OF THE INVENTION

The present invention is a multiple electrode, closed-loop system for the treatment of certain neurological disorders such as epilepsy, migraine headaches and Parkinson's disease. A purpose of the present invention is to overcome the shortcomings of all prior art devices for the treatment of such disorders. Specifically, the present invention combines a multi-electrode array with sophisticated signal processing techniques to achieve reliable detection of the onset of a neurological event (such as an epileptic seizure or migraine headache) typically originating from a focus of limited spatial extent within the brain. It is well known that in certain patients, epileptic seizures consistently originate from a single location within the brain. However, the system described herein is also adaptable for the treatment of a neurological event that involves a major portion or possibly all of the brain tissue.

The present invention also provides means for generating an ensemble of coordinated electrical stimuli designed to terminate the neurological event immediately upon (or even prior to) its onset. Thus, the present invention is a responsive detection and stimulation system for the early recognition and prompt treatment of a neurological event.

The present invention envisions a multiplicity of brain electrodes placed either within the brain, on the surface of the brain itself, or on the dura mater that surrounds the brain. Some one, several, or all of these brain electrodes can be used for detection of an abnormal neurological event such as an epileptic seizure. A responsive stimulation signal can also be applied to any one, several, or all elements of such an electrode array. The responsive stimulation signals sent to each electrode may be identical or they may be programmed to differ in amplitude, frequency, waveform, phase, and time duration. It is also envisioned that sensing electrodes may be entirely separate from the electrodes used for responsive stimulation.

The present invention envisions that a neurological event can be reliably detected in the presence of a normal EEG signal and in the presence of external noise by the use of modern and sophisticated signal processing techniques. Specifically, the electrical signal from an epileptic focus within a specific and limited spatial region within the brain can be reliably detected by combining the signals received at different electrodes that are placed at different distances from the epileptic focus. To improve signal-to-noise ratio, the signal received at a specified location that is at a specific distance from the epileptic focus could have a specific time delay to account for the propagation time it takes for the signal to reach that electrode. For example, if a first electrode is located directly over the site of the epileptic focus and a second electrode is located at a distance of several centimeters from the focus, then to combine these two signals together to optimize detection of a neurological event, the signal at the first (closest) electrode must have an added time delay to account for the time required for the signal to arrive at the position of the second electrode. Thus cross-correlation of EEG signals in the time domain is envisioned to be within the scope of the present invention.

It is also envisioned that appropriate selection (i.e., location) of electrode sites can be used to enhance the reliability for detection and termination of a neurological event. Thus, the present invention envisions enhancement of detection by the use of the spatial domain as it applies to the positioning of detection and treatment electrodes.

Finally, the present invention also envisions signal-to-noise enhancement for optimizing the detection of neurological events by searching for signals in a particular frequency domain. For example, a low-pass filter that excludes signals above 5 Hz could be used to enhance the reliability for detection of a neurological event for certain patients. In addition, detection may be enhanced by first conditioning the EEG signals using programmable, multiple step, signal processing. The processing steps that are envisioned for this signal conditioning include signal summing, squaring, subtracting, amplifying, and filtering.

It is also envisioned that any combination of techniques for signal detection in the time, spatial or frequency domain could be used for providing a highly reliable system for the detection of a neurological event.

The present invention envisions four different modalities for stopping the progression of a neurological event such as an epileptic seizure once it has been detected. A preferred method is to provide a responsive stimulation electrical signal, a second method is to release medication in response to the detection of an event, a third method is to provide an electrical short circuit in the vicinity of the epileptic focus to prevent the occurrence of a full epileptic seizure and a fourth method is the application of a sensory input through normal sensory pathways. Such sensory input could be acoustic (sound input), visual (light input), or other sensory input such as mechanical vibration or electrical stimulation of the skin. Of course it is envisioned that any two or more of these modalities can be used in combination in order to preclude, prevent or decrease the severity of a neurological event such as an epileptic seizure, migraine headache, Parkinson's disease tremor, etc. A valuable attribute of the present invention is the ability to record the EEG signal from any one or all of the detection electrodes. Typically the EEG signal would be continuously recorded in a first-in first-out (FIFO) digital data recording system where the current data overwrites the oldest data as memory storage capacity is exceeded. In the event that a neurological event was detected, the device would save the preceding several minutes of data while continuing to record subsequent EEG data after the application of a response such as responsive stimulation, short circuiting of some electrode(s) or the delivery of a bolus of medication. It is conceived that the device would hold in memory the recording made for several minutes both before and after the neurological event. These data would then be read out by the patient's physician on a regular basis (e.g., every three months, or more frequently if the device did not promptly terminate some neurological event). It is also anticipated that the patient could use a patient's initiating device to trigger the retention of several minutes of data recording of the EEG signal from a pre-selected group of electrodes.

It is also conceived that certain other data be recorded that can be helpful to the physician for treating the patient. These additional data would include: (1) the number of neurological events detected since the last memory readout and; (2) the number of responses triggered by the neurological events that were delivered to the patient. Furthermore, the system can be programmed so that when a neurological event is detected, the electrical signal from any one or more of the multiple steps in the signal conditioning can be stored in a digital memory. Additionally, telemetry would be provided to the physician that would indicate the serial number of the device that is implanted in the patient and the date and time that each neurological event or patient initiated recording occurred.

Another valuable attribute of the present invention is the capability to program the functions and parameters of the system to enhance the detection of a neurological event and to optimize the system responses for stopping a neurological event such as an epileptic seizure. Examples of programmable functions and parameters are: (1) the time delay introduced for a signal being received from a specific electrode; (2) the use or non-use of a specific electrode; (3) the frequency response characteristic of the channel assigned to process the signal received from a specific electrode; (4) whether or not a particular electrode is electrically shorted to another electrode or to the metal case of the device after a neurological event has been detected; (5) the amplitude, frequency, duration, phase and wave-form of the response signal delivered to a specific electrode; (6) the allocation of memory for storing EEG signals as received from one or more electrodes; (7) determination as to whether or not the data from a particular electrode will be stored in memory; (8) the amplitude, frequency and time duration of an acoustic, visual, or other sensory input applied to the patient in response to the detection of a neurological event, and (9) the specification of statistical data (histograms) to be recorded; for example, the number of epileptic seizures and/or the number of responsive stimulations delivered since the last memory readout by an attending physician. These are some but not all of the programmable functions and parameters that the system might utilize.

It should be understood that a telemetry signal would be transmitted from the implanted device. External receiving equipment typically located in the physician's office, would process that signal and provide a paper print-out and a CRT display to indicate the state to which all the parameters of the implanted device have been programmed. For example, the display would indicate which electrodes are active, what algorithm is being used for detection, what specific bandwidth is being used with a specific electrode, etc.

It should be understood that, unlike implantable automatic heart defibrillators which generate a responsive signal only after ventricular fibrillation has occurred, it is a goal of the present invention to prevent full development of an epileptic seizure or migraine headache before the actual occurrence of such an unwanted neurological event. In this regard, the present invention is entirely different from any implantable medical device (such as an automatic heart defibrillator) that always allows the unwanted event to occur.

A specific capability of this system is to provide electrical stimulation to a specific portion of the brain as the means of stopping a neurological event. It is believed that the earliest possible detection of a seizure and treatment of aberrant electrical activity from an epileptic focus has the highest probability of aborting the occurrence of a full seizure. It is envisioned that either through specific placement of treatment electrodes or by adjusting the phase of signals applied to an array of electrodes, stimulation can be directed to the location(s) within the brain that offer the highest probability of stopping the seizure.

It is believed that there is minimal or no effect if a responsive stimulation is produced from an erroneously identified event, i.e., a false positive. On the other hand, failure to identify a real event is highly undesirable and could cause the patient to undergo a severe seizure. Therefore, the design concept of the current invention is to predispose the decision-making algorithm to never miss a real event while allowing a false positive rate to be detected at up to 5 times the rate of actual events.

Telemetry data transmitted from the implanted device can be sent to a physician's workstation in the physician's office either with the patient in the physician's office or remotely from the patient's home by means of a modem. The physician's workstation can also be used to specify all of the programmable parameters of the implanted system.

A novel aspect of a preferred embodiment of this invention is that the entire implantable portion of this system for treating neurological disorders lies under the patient's scalp. Such placement will either have the device located between the scalp and the cranium or the within a hole in the cranium. Because of size constraints, the intracranial location is the preferred embodiment.

The implantable portion of the system includes; (1) electrodes that lie in close proximity to or actually within the brain; (2) a control module that contains a battery and all the electronics for sensing, recording and controlling brain activity, (3) electrically conducting wires that connect the control module to the electrodes, (4) a buzzer providing an acoustic signal or electrical "tickle" indicating that a neurological event has been detected, and (5) an input-output wire coil (or antenna) used for communication of the implanted system with any and all external equipment. The battery that provides power for the system and an electronics module are both contained within a metal shell that lies under the patient's scalp. The metal shell that contains the electronics module and the battery collectively form the control module.

All electrodes connect by means of electrically conducting wires to electrical terminals that are formed into the metal shell. The electronics module is electrically joined to the brain electrodes by means of the shell's electrical terminals, which are electrically joined to the wires that connect to the brain electrodes.

An important aspect of the preferred embodiment of this device is the fact that the shell containing the electronics module and the battery, i.e. the control module, is to be placed in the cranium of the skull at a place where a significant volume of bone is removed. By placing the entire system within the cranium, (as opposed to having some wires extending into or through the neck to a control module in the chest) the probability of wire breakage due to repeated wire bending is drastically reduced. However, the present invention also envisions the placement in the chest or abdomen of a control module if a large battery or a large volume electronics module dictates such a large size for the control module that it cannot be conveniently placed within the cranium. Such a thoracic or abdominal placement of a control module would require wires to be run through the neck.

The present invention also envisions the utilization of an intracranial system for the treatment of certain diseases without placing wires through the neck. Specifically, an alternative embodiment of the invention envisions the use of electrodes in or on the brain with an intracranial control module used in conjunction with a remote sensor/actuator device. For example, blood pressure could be sensed with a threshold of, let us say 150 mm Hg, and if that pressure was exceeded, a signal transmitted by electrical conduction through the body from the remote sensor/actuator device could be received at the control module and that would cause brain stimulation in such a way as to reduce the blood pressure. Conversely, if the brain detects pain and provides a signal detectable by the intracranial system, a signal could be sent by electrical conduction through the body to a remote sensor/actuator device that could provide electrical stimulation to locally stimulate a nerve to reduce the perception of that pain. Still another example is that if the precursor of an epileptic seizure is detected, a remote actuator could be used to electrically stimulate one or both vagus nerves so as to stop the epileptic seizure from occurring. Such a remote device could be located in the trunk of the patient's body.

Another important aspect of this invention is that a comparatively simple surgical procedure can be used to place the control module just beneath the patient's scalp. A similar simple procedure can be used to replace just the battery or both the battery and the electronics module. Specifically, if the hair on the scalp is shaved off at a site directly over where the control module is implanted, an incision can then be made in the scalp through which incision a depleted battery can be removed and replaced with a new battery, or a more advanced electronics module can replace a less capable or failed electronics module. The incision can then be closed, and when the hair grows back, the entire implanted system would be cosmetically undetectable. A good cosmetic appearance is very important for the patient's psychological well-being.

The manner in which the control module, the electrodes and the interconnecting wires are placed beneath the scalp is important for the successful implantation of the entire implantable system. Specifically, the control module is optimally placed in either the left or right anterior quadrant of the cranium. Because the large sagittal sinus vein runs along the anterior-posterior centerline of the cranium, it is inadvisable to run epidural wires through that region, and furthermore, it would be inadvisable to place the control module directly over that major vein. Since movement of the jaw causes motions of the scalp relative to the cranium, it is advisable to run the connecting wires for electrodes that must be placed on the anterior portion of the brain in the epidural space as opposed to running them between the scalp and the cranium. Since the middle meningeal artery and its branches run within grooves interior to the posterior section of the cranium, it would be inadvisable to connect to posterior placed electrodes by utilization of connecting wires positioned in the epidural space beneath the posterior portion of the cranium. Therefore, the connecting wires for electrodes to be placed on a posterior portion of the brain's surface are best located beneath the scalp, then through burr holes in the cranium where they connect to any electrodes placed in a posterior position on the surface of the dura mater. Conversely, most of the length of the connecting wires for electrodes located in the anterior portion of the brain would be placed in the epidural space. In no case should epidural wires be passed through the anterior-posterior centerline of the brain where the large sagittal sinus vein is located.

An important operational aspect of the implanted system is the use of an input-output coil formed from many turns of fine wire that is placed between the scalp and the cranium generally along the anterior-posterior centerline of the head. All communication between the external equipment and the implanted system can be accomplished by magnetic induction through the hair and scalp of the patient. Examples of these signals are the readout of telemetry from the implanted system, or the changing of some operational parameter of the implanted system by means of a command from some piece of external equipment. Furthermore, such an input-output coil can be used to recharge a rechargeable battery that can be located inside the control module. Since the input-output coil can be placed on a posterior portion of the cranium, relative motion of the scalp and cranium should not be a problem in that region.

By placing the input-output coil in an appropriate site just beneath the scalp, the patient can be provided with a cap to be worn on the head which cap includes a flexible coil that can communicate by magnetic induction using an alternating magnetic field with the implanted input-output coil. Such a cap could be placed on the patient in the doctor's office when the doctor wishes to read out stored telemetry or program one or more new parameters into the implanted system. Furthermore, the cap could be used by the patient at home for remote connection to the physicians workstation over telephone lines using a pair of modems, or the cap could be used to recharge a rechargeable battery located in the control module of the implanted system.

Another important aspect of the system is a buzzer that can be implanted just behind the ear on the outer or inner surface of the cranium or actually within a burr hole within the cranium. The buzzer may be any sound-emitting or vibration-generating device such as a piezoelectric crystal that can convert electrical signals sent from the control module into vibrations that can be picked up through bone conduction (or through the air) by the patient's ears, particularly the inner ears. If a neurological event is detected, the buzzer can provide an acoustic output that is detectable by the patient's ear or the buzzer can provide an electrical "tickle" signal. The acoustic output can be, for example, a buzz, a tone, a sequence or combination of tones, a synthesized or reproduced complex sound, or a segment of human speech. The buzzer can be used to indicate to the patient that a neurological event such as an epileptic seizure is about to occur so that an appropriate action can be taken.

In contrast to cochlear implant-type devices, the buzzer or acoustic transducer of the present invention is designed to provide audible information via vibrations to a person with an ordinary (or functional) level of hearing. Moreover, a device according to the invention would generate specific sounds, as set forth above, and generally would not amplify external ambient sound for transmittal to and electrical stimulation of the middle or inner ear (as in a cochlear implant).

Among the appropriate actions that could be taken by the patient is the application of an acoustic, visual or sensory input that could, by itself, be a means for stopping a neurological event such as an epileptic seizure. The acoustic input could be by means of a sound producing, hearing aid shaped device that can emit an appropriate tone or voice announcement directly into the ear. The visual device could be from a light emitting diode in eyeglasses or a small flashlight type of device that emits a particular type of light at some appropriate flashing rate. A sensory input could be provided by, for example, an externally mounted electrical stimulator placed on the wrist to stimulate the median nerve or by a mechanical vibrator applied to the patient's skin.

As one embodiment of the control module is implanted into the cranium, a buzzer attached to the inside of the control module case would produce vibrations conducted by the case to the cranium and detectable by the patient's ears.

The acoustic signal that can be sent to the "buzzer" need not be just a tone or buzz but could be a complex sound or a segment of encoded human speech stored in the memory of the control module or transmitted from the external equipment to the control module. The buzzer would typically be a small acoustic transducer such as a piezoelectric crystal or a miniature loudspeaker, e.g. from a hearing aid. Speech segments could be stored in digital memory of the control module using encoding methods including (but not limited to) pulse code modulation (PCM), adaptive differential pulse code modulation (ADPCM), or linear predictive coding (LPC) and played out through a digital-to-analog converter to the buzzer. If the output of the digital-to-analog converter is insufficient to drive the acoustic transducer, an amplifier may be used to increase the signal strength.

Similarly, a complex sound can be generated as an electrical signal by known analog or digital sound synthesis methods or by known analog or digital sound reproduction methods.

The ability to communicate with the patient from a device implanted under the scalp has applications beyond notification of detected neurological events. Such communication can be reminders to the patient to take medications, warnings that the device battery is low and needs recharging or replacement, or a daily notification that the system is functioning properly. If the control module is acting only as a neurological event detector without electrical stimulation, the announcement could warn the patient to sit down or otherwise stop activities because a seizure is about to begin. With the ability to detect the precursor to a neurological event, an alert to take medication could be extremely effective in averting a seizure.

The control module of the present invention also has wireless external communication capability that could be combined with the ability to allow external equipment to initiate the signals played to the patient by the acoustic transducer. Such signals could include instructions for downloading stored EEG data through a modem to the patient's doctor. Other signals of interest for the present invention could be the ringing or voice signals received by a telephone or an alarm generated by external equipment.

It is also well known that many types of acoustic transducers can also act as microphones. As such, the buzzer could allow direct voice communication from the patient to the control module. The control module already having digital signal processing and pattern recognition capabilities could be programmed to recognize the patient's speech. Another way for the patient to signal the control module might be by simply tapping near the transducer. For instance 5 taps might signal the control module to begin a sequence of prompts that can be answered, one tap for yes two taps for no.

As the brain becomes more and more directly coupled to implanted and external computers, the ability to communicate directly with the patient via implantable devices will be an important capability. Such communication could also be linked to remote modules that could sense blood pressure, temperature, heart electrical activity, blood oxygen or any other internal body measurement.

The present invention with microphone and loudspeaking ability could also provide an implanted interface to a communications device such as a telephone or two-way radio.

When any such acoustic, visual or other sensory input is actuated, either automatically or manually in response to the detection of a neurological event, literally billions of neurons are recruited within the brain. The activation of these neurons can be an effective means for stopping an epileptic seizure.

An alternative embodiment of the present invention envisions the use of a control module located external to the patient's body connected to electrodes either external or internal to the patient's scalp. Such an externally located control module might be positioned behind the patient's ear like a hearing aid.

Thus it is an object of this invention to provide appropriate stimulation of the human brain in response to a detected neurologic event in order to cause the cessation of that neurologic event.

Another object of this invention is to provide increased reliability for neurological event detection by the use of cross-correlated signals from multiple electrodes with appropriate time delay(s) to increase the sensitivity and reliability for detection from a specific area of the brain.

Still another object of this invention is to exploit a spectral characteristic of the signals from multiple electrodes to optimize the detection of a neurological event.

Still another object of this invention is to predispose the decision-making algorithm to allow false positives to cause a responsive stimulation but to disallow missing an actual event.

Still another object of this invention is to have the response to a neurological event be an electrical stimulation that is focused on a specific area of the brain by variably delaying the stimulation signal sent from each of several stimulation electrodes placed at different locations placed in close proximity to the brain or within the brain.

Still another object of this invention is to have the specific area of the brain onto which the response is focused be the area from which the event signal was detected.

Still another object of this invention is to record (and ultimately recover for analysis) the EEG signal(s) from one or more electrodes before, during and after a neurological event.

Still another object of this invention is to provide programmability for all-important operating parameters of the device.

Still another object of this invention is to provide recording of the certain functions of the device such as how many neurological events were detected and how many times the device responded to such detections.

Still another object of this invention is to use medication delivery as the response to a neurological event, either alone or in conjunction with electrical stimulation.

Still another object of this invention is to utilize implanted electronic circuitry that is adaptable to changing EEG input signals so as to provide self-adaptation for the detection and/or treatment of a neurological event.

Still another object of this invention is to have a system of electrodes connected by wires to a control module, the entire system being placed under the scalp and being essentially contained within the cranium.

Still another object of this system is to have essentially no flexure of interconnecting wires so as to enhance system reliability.

Still another object of this invention is to be able to replace a depleted battery within the system's control module by a comparatively simple and quick surgical procedure.

Still another object of this invention is to be able to replace an electronics module within the system's control module by a comparatively simple and quick surgical procedure.

Still another object of this invention is to be able to recharge the battery in the control module.

Still another object of this invention is to provide an externally situated patient's initiating device that can be used by the patient when he or she senses that a neurological event is about to occur in order to provide a response for causing the stopping of that neurological event or in order to initiate the recording of EEG signals from a pre-selected set of electrodes.

Still another object of this invention is to utilize a remotely located sensor/actuator device within the body to detect an abnormal physiological condition and send an electrical signal with or without wires to a control module within the cranium, which then responds, by an electrical signal delivered to the brain to treat the abnormal physiological condition.

Still another object of this invention is to utilize an intracranial system for sensing some abnormal physiological condition and then sending an electrical signal with or without wires to a remote sensor/actuator device that is remotely located within the body to carry out some treatment modality.

Still another object of this invention is to provide a buzzer that indicates to the patient that a neurological event has occurred.

Still another object of this invention is to have the buzzer alert the patient to take medication to stop or reduce the severity of a detected event.

Still another object of this invention is to have the buzzer communicate with the patient by transducing voice announcements into acoustic signals detectable by the patient's ears.

Still another object of this invention is to have the buzzer also act as a microphone to pick up patient speech or taps used to signal the control module.

Still another object of this invention is to have the buzzer implanted in proximity to the cranium so that mechanical vibrations from the buzzer are detectable by the patient's ears.

Still another object of this invention is to have the voice announcements encoded and stored in digital memory within the control module.

Still another object of this invention is to provide acoustic, visual or other sensory inputs to the patient either automatically or manually following the detection of a neurological event so as to stop the neurological event.

These and other objects and advantages of this invention will become apparent to a person of ordinary skill in this art upon careful reading of the detailed description of this invention including the drawings as presented herein.

DETAILED DESCRIPTION OF THE INVENTION

Figure 1:
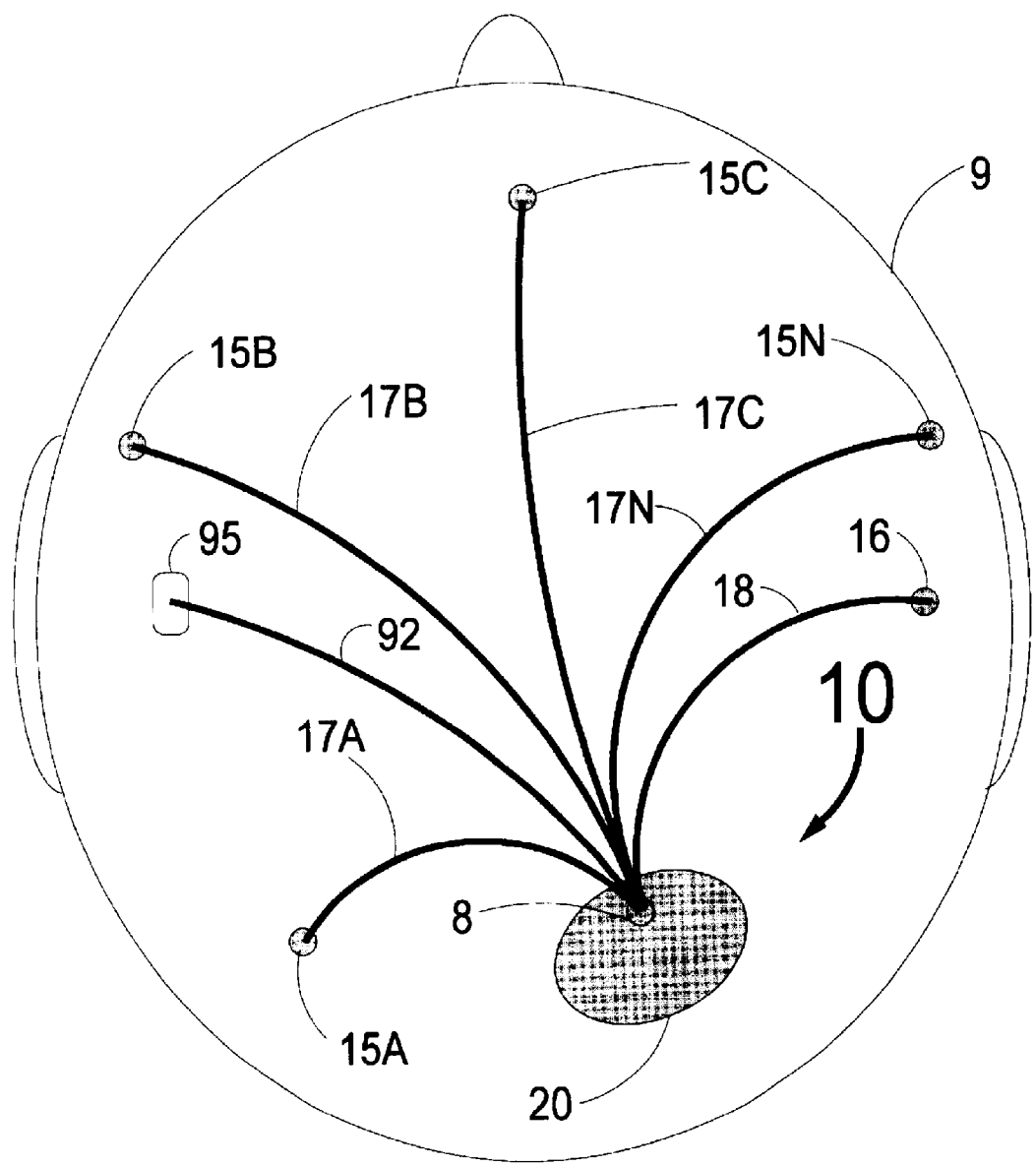
FIG. 1 is a top view of a human head showing the configuration of an implantable system for the treatment of neurological disorders, as it would be situated in the human skull.

FIG. 1 illustrates the configuration of an implantable system 10 for the treatment of neurological disorders as it would be situated under the scalp of a human head 9 having a control module 20, electrodes 15A, 15B, 15C, 15N and 16 with wires 17A, 17B, 17C, 17N and 18 connected through the connector 8 to the control module 20. It is envisioned that the control module 20 is permanently implanted into the top of the skull in a location where the skull is fairly thick. It is also envisioned that the control module 20 could be located in the trunk of the patient's body like a heart pacemaker with the connecting wires being run under the patient's skin. The electrodes 15A, 15B, 15C, 15N and 16 would be placed under the cranium and above the dura mater (i.e., placed epidurally) or placed deep into the brain. The connecting wires 17A, 17B, 17C, 17N and 18 would be run from the control module 20 underneath the scalp and then be connected to the electrodes placed beneath the patient's cranium. Although FIG. 1 shows only 4 active electrodes 15A, 15B, 15C, 15N with connecting wires 17A, 17B, 17C, 17N, more than 4 active electrodes with connecting wires may be used with the present invention. The electrode 16 (having a connecting wire 18) could be considered a common or indifferent electrode.

Throughout this detailed description of the present invention, the terminology "the electrodes 15A through 15N" is meant to include all electrodes 15A, 15B, 15C, ..., 15N, inclusive, where N may be any integer between 1 and 200. Similar terminology using the words "through" or "to" for other groups of objects (e.g., "wires 17A through 17N") will have a similar inclusive meaning.

Throughout FIGS. 1 through 25 inclusive, lines connecting boxes on block diagrams or on software flow charts will each be labeled with an element numeral. Lines without arrows between boxes and/or solid circles indicate a single wire.

Lines with arrows connecting boxes or circles are used to represent any of the following:
1. A physical connection, namely a wire or group of wires (data bus) over which analog or digital signals may be sent.
2. A data stream sent from one hardware element to another. Data streams include messages, analog or digital signals, commands, EEG information, and software downloads to change system operation and parameters.
3. A transfer of information between software modules. Such transfers include software subroutine calls with and without the passing of parameters, and the reading and writing of memory locations.

In each case, the text will indicate the use of the line with an arrow.

Figure 2:
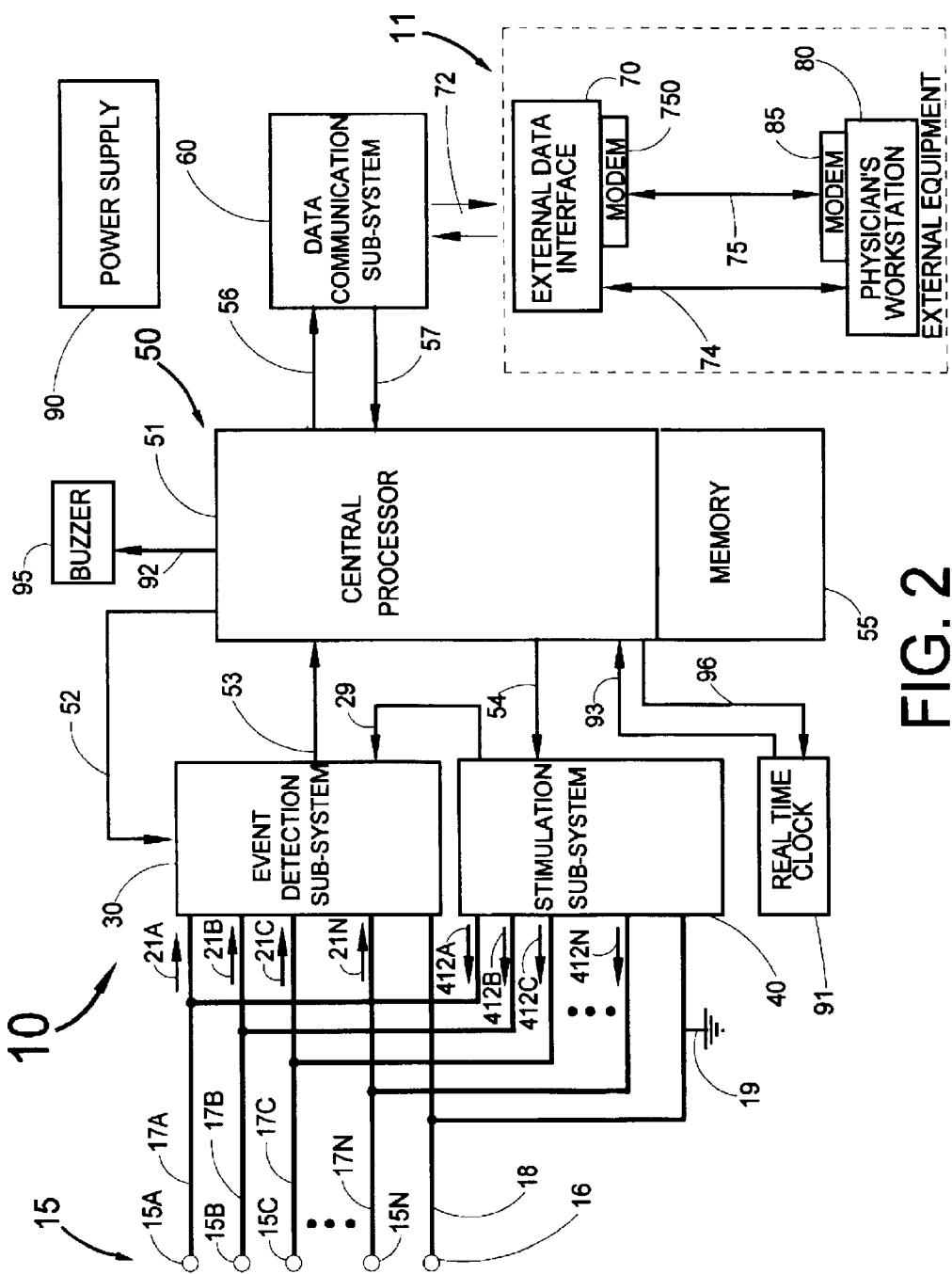
FIG. 2 is a block diagram of the implanted and external portions of the system.

FIG. 2 is a block diagram of the implantable system 10 and the external equipment 11. The wires 17A through 17N from the electrodes 15A through 15N, and the wire 18 from the common electrode 16, are shown connected to both the event detection sub-system 30 and the stimulation sub-system 40. It is also envisioned to use the case of the control module 20 of FIG. 1 as the common (or indifferent) electrode 16. The wires 17A through 17N carry EEG signals 21A through 21N from the electrodes 15A through 15N to the event detection sub-system 30. The electrodes 15A through 15N can be energized by the stimulation sub-system 40 via the wires 17A through 17N to electrically stimulate the patient's brain using the stimulation signals 412A through 412N respectively. Although the electrodes 15A through 15N and 16 shown here are connected to both the event detection sub-system 30 and the stimulation sub-system 40, it is obvious that a separate set of electrodes and associated wires could be used with each sub-system. Furthermore, it is envisioned that any one, several or all of the electrodes 15A through 15N could be electrically connected (i.e., shorted) to the electrode 16 or to each other. This would be accomplished by appropriate switching circuitry in the stimulation sub-system 40.

The event detection sub-system 30 receives the EEG signals 21A through 21N (referenced to system ground 19 connected to the wire 18 from the common electrode 16) and processes them to identify neurological events such as an epileptic seizure or its precursor. A central processing system 50 with central processor 51 and memory 55 acts to control and coordinate all functions of the implantable system 10. The interconnection 52 is used to transmit programming parameters and instructions to the event detection sub-system 30 from the central processing system 50. The interconnection 53 is used to transmit signals to the central processing system 50 identifying the detection of a neurological event by the event detection sub-system 30. The interconnection 53 is also used to transmit EEG and other related data for storage in the memory 55.

When an event is detected by the event detection sub-system 30, the central processor 51 can command the stimulation sub-system 40 via the interconnection 54 to transmit electrical signals to any one or more of the electrodes 15A through 15N via the wires 17A through 17N. It is anticipated that, if appropriate electrical signals 412A to 412N inclusive are transmitted to certain locations in or near the brain, the normal progression of an epileptic seizure can be aborted. It may also be necessary for the stimulation sub-system 40 to temporarily disable the event detection sub-system 30 via the interconnection 29 when stimulation is imminent so that the stimulation signals are not inadvertently interpreted as a neurological event by the event detection system 30.

A power supply 90 provides power to each component of the system 10. Power supplies for comparable implantable devices such as heart pacemakers and heart defibrillators are well known in the art of implantable electronic devices. Such a power supply typically utilizes a primary (non-rechargeable) storage battery with an associated DC-to-DC converter to obtain whatever voltages are required for the implantable system 10. However, it should be understood that the power supply could use a rechargeable battery that is charged by means of a coil of wire in the control module 20 that receives energy by magnetic induction from an external coil that is placed outside the patient but in close proximity to the control module. The implanted coil of wire could also be located remotely from control module 20 but joined to it by electrical wires. Such technology is well known from the rechargeable cardiac pacemaker. Furthermore, the same pair of coils of wire could be used to provide power to the implanted system 10 when it is desired to read out stored telemetry or reprogram some portion of the implanted system 10.

Data stored in the memory 55 can be retrieved by the patient's physician via a wireless communication link 72 with the data communication sub-system 60 connected to the central processing system 50. An external data interface 70 can be directly connected with an RS-232 type serial connection 74 to the physician's workstation 80. Alternately, the serial connection may be via modems 85 and 750 and phone line 75 from the patient's home to the physician's workstation 80. The software in the computer section of the physician's workstation 80 allows the physician to read out a history of events detected including EEG information before, during, and after the event as well as specific information relating to the detection of the event such as the time evolving energy spectrum of the patient's EEG. The workstation 80 also allows the physician to specify or alter the programmable parameters of the implantable system 10.

The external data interface could be a specially designed unit or preferably a modified off-the-shelf computer. Such an off-the-shelf computer could be a desktop, laptop or palmtop type PC or a PDA such as the 3COM Palm Pilot VII that has both display and built in Internet data communication capability. The modem 70 could also be a standard phone line modem, or a cable or DSL modem allowing direct high-speed access to the Internet.

As shown in FIGS. 1 and 2, a buzzer 95 connected to the central processor 51 via the link 92 can be used to notify the patient that an event has occurred or that the implanted system 10 is not functioning properly. The buzzer could provide a mechanical vibration (typically an acoustic signal) or an electrical stimulation "tickle" either of which could be perceived by the patient. By placing the buzzer 95 near the ear and on the top of, below, or within a burr hole in the cranium, an acoustic signal emitted by the buzzer 95 will be detectable by the patient's ear. This sound by itself can be an automatic means for stopping an epileptic seizure.

The acoustic signal delivered by the buzzer 95 can be a buzz, a tone, a sequence or combination of tones, a segment of recorded music, a synthesized or reproduced complex sound, or a segment of human speech. The speech could be either synthesized human speech or recorded and digitally encoded human speech stored in the memory of the control module or transmitted from the external equipment to the control module. The buzzer 95 would typically be a small acoustic transducer such as a piezoelectric crystal or a miniature loudspeaker, e.g. from a hearing aid. The speech segments could be stored in digital memory of the control module using encoding methods such as PCM or ADPCM and played out through a digital-to-analog converter to the buzzer.

Speech synthesis integrated circuits that can convert text into human speech are well known and could be used instead of recorded speech so that the voice announcements could be stored as text strings instead of encoded voice recordings.

The ability to communicate with the patient from a device implanted under the scalp or intracranially has applications beyond notification of detected neurological events. Such communication can be reminders to the patient to take medications, warnings that the device battery is low and needs recharging or replacements or just a daily notification that the system is functioning properly. If the control module 20 is acting only as a neurological event detector without stimulation, the announcement could tell the patient to sit down or stop activities because a seizure is about to begin. With the ability to detect the precursor to a neurological event, an alert to take medication could be extremely effective in averting a seizure.

The control module 20 of the present invention also has a wireless external communication link 72 that could allow external equipment to initiate the acoustic signals played to the patient by the buzzer. Such signals could include instructions for downloading stored EEG data stored in the memory 55 through the modem 750. Other signals of interest for the present invention could be the ringing or voice signals received by a telephone or an alarm generated by the external equipment 11.

A real time clock 91 is used for timing and synchronizing various portions of the implanted system 10 and also to enable the system to provide the exact date and time corresponding to each neurological event that is detected by the implantable system 10 and recorded in memory. The interconnection 96 is used to send data from the central processor 51 to the real time clock 91 in order to set the correct date and time in the clock 91.

The various interconnections between sub-systems (e.g., the interconnections 52, 53, 54, 56, 57, 92, 93 and 96) may be either analog or digital, single wire or multiple wires (a "data bus").

The operation of the system 10 of FIG. 2 for detecting and treating a neurological event such as an epileptic seizure would be as follows:

1. The event detection sub-system 30 continuously processes the EEG signals 21A through 21N carried by the wires 17A through 17N from the N electrodes 15A through 15N.
2. When an event is detected, the event detection sub-system 30 notifies the central processor 51 via the link 53 that an event has occurred.
3. The central processor 51 then triggers the stimulation sub-system 40 via the link 54 to electrically stimulate the patient's brain (or electrically short some electrodes or release medication) in order to stop the neurological event using any one, several or all of the electrodes 15A through 15N.
4. The stimulation sub-system 40 also sends a signal via the link 29 to the event detection sub-system 30 to disable event detection during stimulation to avoid an undesired input into the event detection sub-system 30.
5. The central processor system 50 will store EEG signals and event related data received from the event detection sub-system 30 via the link 53 over a time from X minutes before the event to Y minutes after the event for later analysis by the patient's physician. The value of X and Y may be set from as little as 0.1 minutes to as long as 30 minutes.
6. The central processor 51 may "buzz" to notify the patient that an event has occurred by sending a signal via the link 92 to the buzzer 95.

Figure 3:
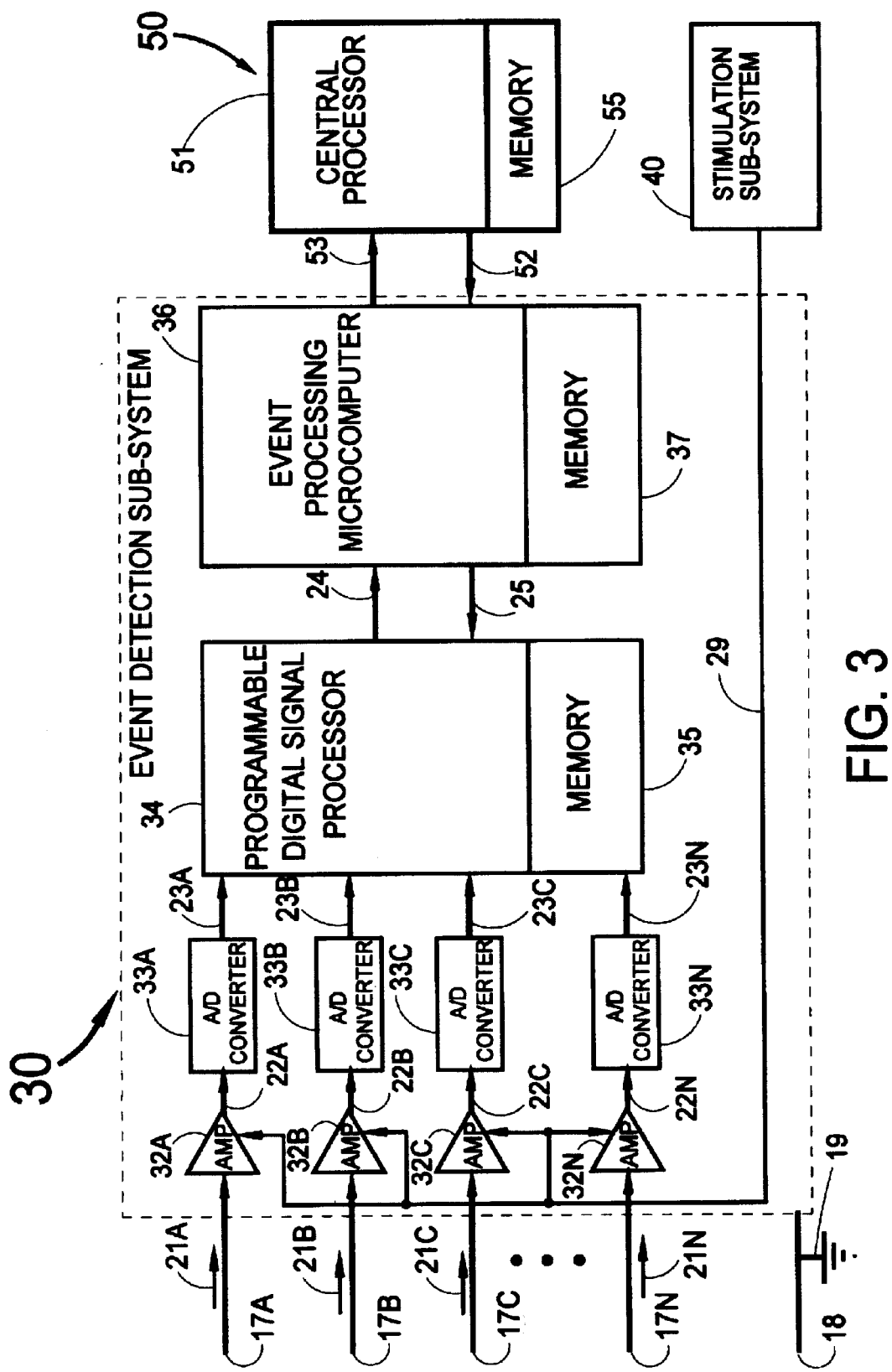
FIG. 3 is a block diagram illustrating the event detection sub-system that utilizes digital signal processing techniques that can exploit either or both time and frequency domain information to accomplish event detection.

FIG. 3 is a block diagram illustrating an implementation of the event detection sub-system 30 using digital signal processing techniques. The event detection sub-system 30 can use either or both, time and frequency domain information for event detection. The event detection sub-system 30 receives the signals 21A through 21N from the wires 17A through 17N and processes them to identify the early stages of a neurological event such as an epileptic seizure. The signals 21A through 21N are amplified by the amplifiers 32A through 32N respectively, to produce the amplified EEG signals 22A through 22N. The amplifiers 32A through 32N can also provide low pass and/or high pass filtering to remove unwanted noise. Each amplifier 32A through 32N can be disabled by a signal placed on interconnection 29 from the stimulation sub-system 40 during brain stimulation so as to prevent overloading the amplifiers or creating an undesired input signal into the event detection sub-system 30.

The amplified EEG signals 22A through 22N are then digitized by the analog-to-digital converters 33A through 33N producing the digitized EEG signals 23A through 23N which are processed by the programmable digital signal processor 34 with associated memory 35 to enhance the signal-to-noise ratio for the detection of neurological events. Processed signals 24 are then passed to the event processing microcomputer 36 with associated memory 37 for analysis with the goal of achieving event detection. When the event processing microcomputer 36 identifies an event, it produces a detection signal, which it sends along with stored EEG and EEG energy spectral data streams to the central processor 51 through the interconnection 53. The central processor 51 can pass specific program parameters and revised programming instructions to the event processing microcomputer 36 via the interconnection 52. The event processing microcomputer 36 can also pass any appropriate program parameters and revised programming instructions received from the central processor 51 on to the programmable digital signal processor 34 via the interconnection 25. This scheme provides patient-specific optimization of event detection algorithm (s). For example the program might look at signal amplitude differences between certain electrodes, or alternately, event detection might be based on analysis of a signal created by adding the signals (possibly with varying time delays) derived from a specific subset of the electrodes. It is also possible that the programmable digital signal processor 34 might be programmed to perform both digital signal processing and event processing thus not requiring a separate event processing microcomputer 36. It is also envisioned that the event processing microcomputer 36 and the central processor 51 may be the same microcomputer having separate subroutines in software for each function.

The amplifiers 32A through 32N, the analog-to-digital converters 33A through 33N and the programmable digital signal processor 34 each separately and collectively constitute a signal conditioning means for processing the EEG signals 21A through 21N. The event processing microcomputer 36 provides event detection means for the detection of a neurological event.

Integrated circuit amplifiers, analog-to digital converters, digital signal processors (DSPs), digital memory and microcomputers and the techniques to interconnect and program them are well known in the art. Custom VLSI or hybrid circuits could be developed that would combine certain functions.

Figure 4:
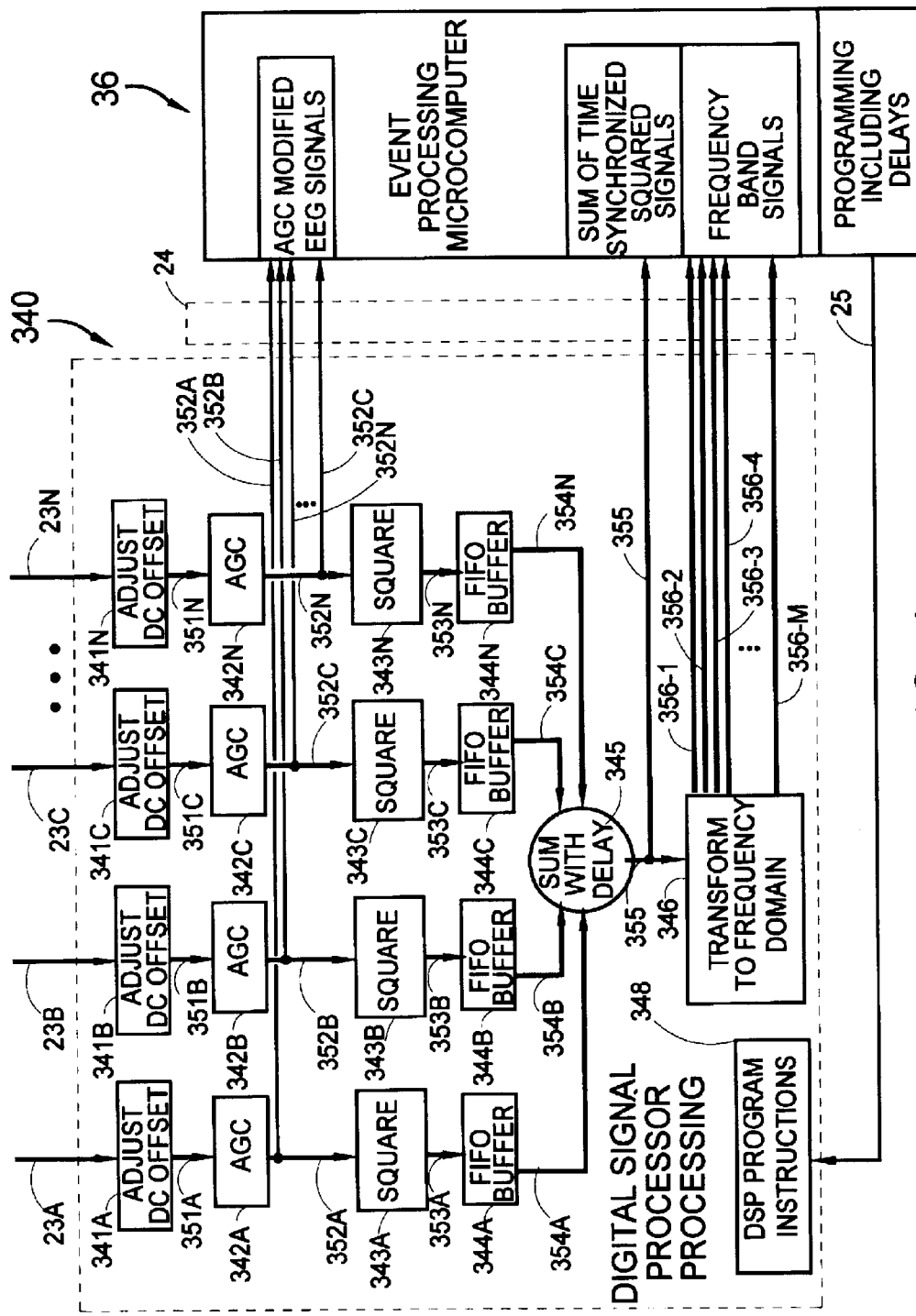
FIG. 4 is a flow chart pertinent to the processing activity carried on within the programmable digital signal processor that is part of the event detection sub-system.

FIG. 4 is a flow chart pertinent to the processing activity 340 carried on within the programmable, digital signal processor 34 of the event detection sub-system 30. The digitized EEG signals 23A through 23N are first processed by the step of removing any d-c bias by the subroutines 341A through 341N producing digital signals 351A through 351N which are then processed by the automatic gain control (AGC) subroutines 342A through 342N to produce the AGC EEG signals 352A through 352N. These AGC EEG signals 352A through 352N would then be free of any d-c bias, and be of identical maximum amplitude during that time when the brain is not experiencing a neurological event.

The purpose of AGC is to remove the variation in EEG signal amplitude that can change slowly over a period of a few hours. Thus the AGC subroutines 342A through 342N might adjust the amplitude of incoming signals 351A through 351N based on the average energy detected over a period of several minutes. However, a rapidly changing signal such as that from a neurological event would not have their amplitudes modified by the AGC subroutines 342A through 342N.

Using the step of AGC at this stage of the processing will allow the use of a constant threshold for event identification at a later stage. The AGC time constant is among the programmable parameters that can be programmed in the DSP program instructions 348 that are passed via the interconnection 25 from the event processing microcomputer 36. AGC algorithms that adjust the output gain based on time-averaged energy are well known in the art and can be implemented by an experienced DSP programmer. It is also envisioned that the amplifiers 32A through 32N of FIG. 3 might be analog AGC amplifiers so that a DSP AGC algorithm would be unnecessary. AGC is an example of a self-adaptive algorithm used by the event detection sub-system 30.

The processed EEG signals 352A through 352N are continuously passed via the interconnections 24 to the event processing microcomputer 36 so that they may be stored for later physician analysis if a neurological event occurs. The processed EEG signals 352A through 352N are also processed further by additional signal conditioning steps to enhance event identification. These steps involve first squaring the signals 352A through 352N using the squaring subroutines 343A through 343N to produce the squared EEG signals 353A through 353N. The squared EEG signals 353A through 353N are fed into the First-In-First-Out (FIFO) buffers 344A through 344N where between 1 and 100 milliseconds of data can be stored. Implementing FIFO data storage in DSP software is well known and can be implemented by an experienced DSP programmer.

Epileptic seizures and many other neurological events can originate in a comparatively small section of the brain called an epileptic focus. A preferred embodiment of the digital signal processing algorithm 340 for event detection is based on the principle that the signals arriving at the electrodes 15A through 15N (shown in FIG. 2) from an epileptic focus will always do so with essentially the same time delay for each electrode. Or stated another way, the propagation time required for a signal to travel from the epileptic focus to an electrode will be consistently as follows: $t_1$ milliseconds for a electrode 15A. $t_2$ milliseconds for electrode 15B, $t_3$ milliseconds for electrode 15C, etc., where $t_1, t_2, t_3 \ldots$ do not significantly change in value from time-to-time. The FIFOs 344A through 344N are nothing more than a digital equivalent of a delay line where the sum with delay algorithm 345 can elect to sample the squared EEG signals 353A through 353N with each delayed appropriately to create the time-synchronized EEG signals 354A through 354N which are summed by the sum with delay algorithm 345. The sum with delay algorithm 345 will produce the sum of time-synchronized squared signals 355. EEG signals originating from parts of the brain away from the focus will not be synchronized by the algorithm 345, the time delays of which are set to synchronize EEG signals originating at the focus. Thus the amplitude of the sum of time-synchronized squared signals 355 will be much larger for EEG signals originating at the focus.

The delays for each of the FIFO buffers are programmed through the DSP program instructions 348. The settings for FIFO time delays would be derived from analysis of recorded EEG signals during events from a patient having the same electrode configuration to be used for event detection. Interconnection 25 is the interconnection over which the programming instructions 348 are provided by the event processing microcomputer 36 to set the time delay parameters for the FIFO buffers.

The signal 355 can be sent to the event processing microcomputer 36 for time domain event detection. The signal 355 can also be transformed into the frequency domain by the transform algorithm 346, which will produce a frequency spectrum that can change with time having frequency band signals 356-1, 356-2, 356-3, 356-4 through 356-M which are the time evolving signals corresponding to a total of M frequency bands (band 1 through band M). The frequency band signals 356-1 through 356-M are digital data streams, each representing the energy of the signal 355 in the corresponding frequency band (band 1 through band M). An example of such frequency bands is as follows: (a) band 1: 1 to 2 Hz; (b) band 2: 2 to 4 Hz; (c) band 3: 4 to 8 Hz; etc. The specific division of the bands is programmable through the DSP programming instructions 348 and may be derived for each patient from analysis of recorded EEG information. The frequency band signals 356-1 through 356-M are sent to the event processing microcomputer 36 for the purpose of event detection.

FIGS. 3 and 4 illustrate one embodiment of a multiple step signal conditioning means for the EEG signals 21A through 21N. The specific steps used in this embodiment are amplification, analog-to-digital conversion, adjustment of DC offset, AGC, squaring, time delaying, summing and frequency transformation. The ability to program the programmable digital signal processor 34 to implement any combination of these or other steps in any order to enhance event detection for each patient is an important aspect of the event detection sub-system 30.

Figure 5A:
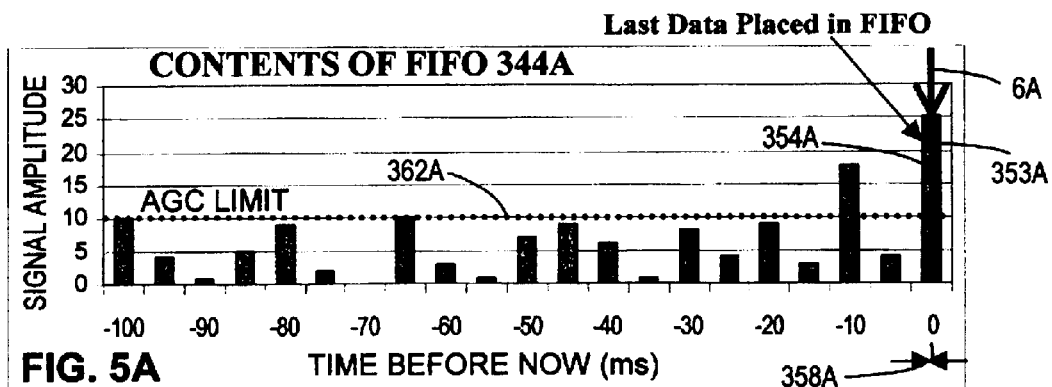
FIG. 5A illustrates the amplitude of the electrical signal received at FIFO memory 344A as a function of time.
Figure 5B:
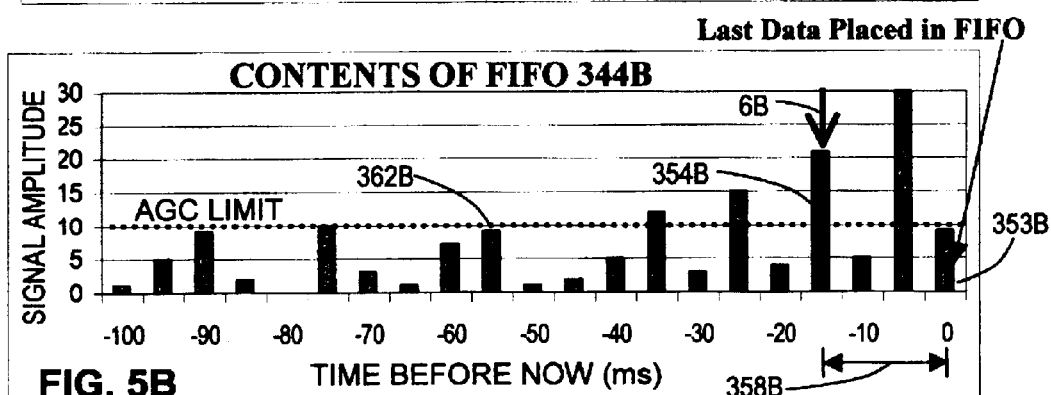
FIG. 5B illustrates the amplitude of the electrical signal received at FIFO memory 344B as a function of time.
Figure 5C:
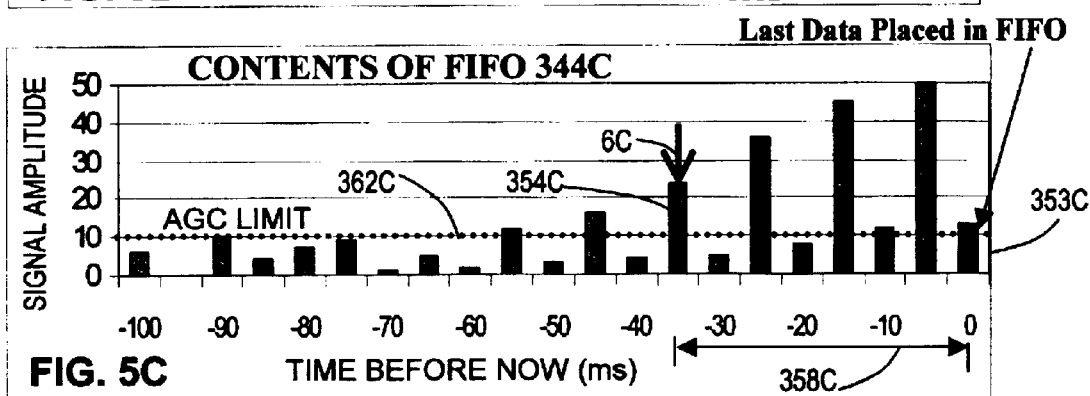
FIG. 5C illustrates the amplitude of the electrical signal received at FIFO memory 344C as a function of time.

FIGS. 5A, 5B and 5C show the signal traces for a 3 electrode implementation of the present invention with the squared EEG signals 353A, 353B and 353C stored in the FIFOs 344A, 344B and 344C respectively. In this example, the FIFOs 344A, 344B and 344C store 100 milliseconds of data consisting of 20 samples each, with each sample being the average value for a period of 5 milliseconds of the squared EEG signals 353A, 353B and 353C. The last data placed in the FIFOs 344A, 344B, and 344C correspond to time equals zero, and are the most recent samples of the squared EEG signals 353A, 353B and 353C.

During pre-implant data recording and analysis of a patient's EEG data, the relative delays between EEG signals from an epileptic focus arriving at electrodes 15A, 15B and 15C would be calculated. In this example, the electrode 15A from which the data in FIFO 344A originates is the last to receive the EEG signal from such an event. The time delay parameter 358A for the electrode 15A is therefore set to 0. In this example, electrode 15B which is the source of data for FIFO 344B, is known to receive an event signal 15 ms before electrode 15A thus the time delay parameter 358B for electrode 15B is set to 15 ms. Similarly, electrode 15C from which the data in FIFO 344C receives an event signal 35 ms before electrode 15A; thus the signal delay parameter 358C for electrode 15C is set to 35 ms.

Figure 5D:
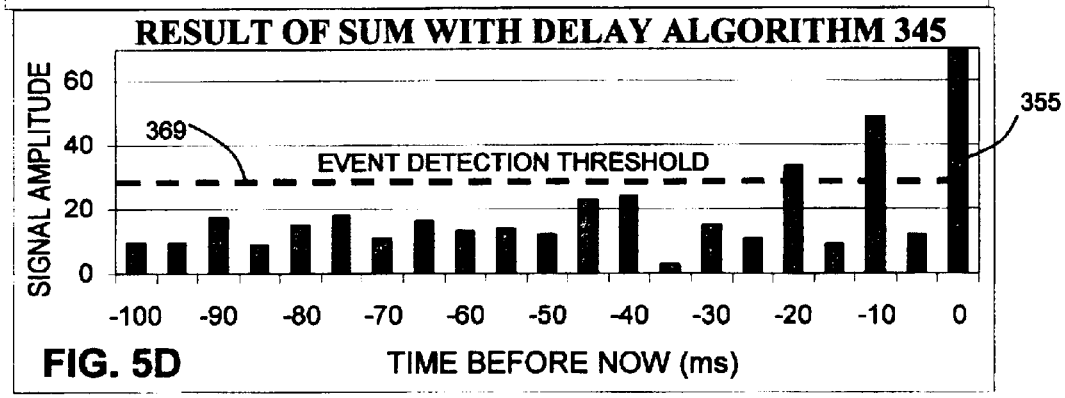
FIG. 5D illustrates the sum of the time delayed signal amplitudes showing also that the event detection threshold is exceeded at −20 milliseconds.

Using the time delay parameters 358A, 358B and 358C, the specific samples 354A, 354B and 354C (marked with the black arrows 6A, 6B and 6C) are fed into the sum with delay algorithm 345. The sum with delay algorithm 345 adds these specific FIFO samples together to produce the signal 355 as shown in FIGS. 4 and 5D. FIG. 5D shows the current sample of the signal 355 and the last 100 milliseconds of the signal 355 created by the sum with delay algorithm 345.

A simple means to detect, a neurological event using the sum with delay algorithm 345 with resulting signal 355 is to compare the signal 355 with a fixed event detection threshold 369 as shown in FIG. 5D. The threshold 369 is exceeded at times 0, −10 ms and −20 ms. This methodology can be an effective means for event detection when used in conjunction with the automatic gain control algorithms 342A, 342B and 342C as shown in FIG. 4. The automatic gain control has the effect which is seen in FIGS. 5A through 5C of keeping the samples of the squared EEG signals below the AGC limits 362A, 362B and 362C which limits are programmed into the automatic gain control algorithms 342A, 342B and 342C shown in FIG. 4. The AGC subroutines 342A, 342B and 342C might adjust the amplitude of the EEG signals 352A through 352N based on the average energy detected over a period of several minutes so that a rapidly changing signal such as that from a neurological event will not be affected.

It is also envisioned that the delay parameters 358A, 358B and 358C may be self-adaptive, so that when an event is detected, post-analysis by the digital signal processor 34 using the data stored in the FIFOs 344A, 344B, and 344C can determine if adjusting the delays 358B and 358C plus or minus in time would increase or decrease the sum of the time-synchronized squared EEG signals 355. If the signal 355 increases by a shift of the time delay 358B or 358C, then the delay parameters 358B and 358C could be automatically changed to increase the sensitivity for future event detection. This example of the capability to modify its own operating parameters is an example of self-adaptation of the programmable digital signal processor 34. It is also envisioned that other programmable components of the system 10 of FIG. 2 other than the event detection sub-system 30 may be self-adaptive to be capable of optimizing system operability without external commands.

Although FIGS. 5A–5D show the signals relating to an implementation of the present invention using 3 signal electrodes, the algorithms described can be applied to any set of 2 or more signal electrodes.

It is also envisioned that instead of delaying the signals from each electrode to provide time synchronization, the electrodes might be placed at positions where the time delays from an epileptic focus to each electrode could be the same. Furthermore, it is envisioned that instead of squaring the value of the EEG signal amplitude, which is done to eliminate a zero average over a certain period of time, the same objective could be accomplished by rectification of the EEG signal.

Figure 6:
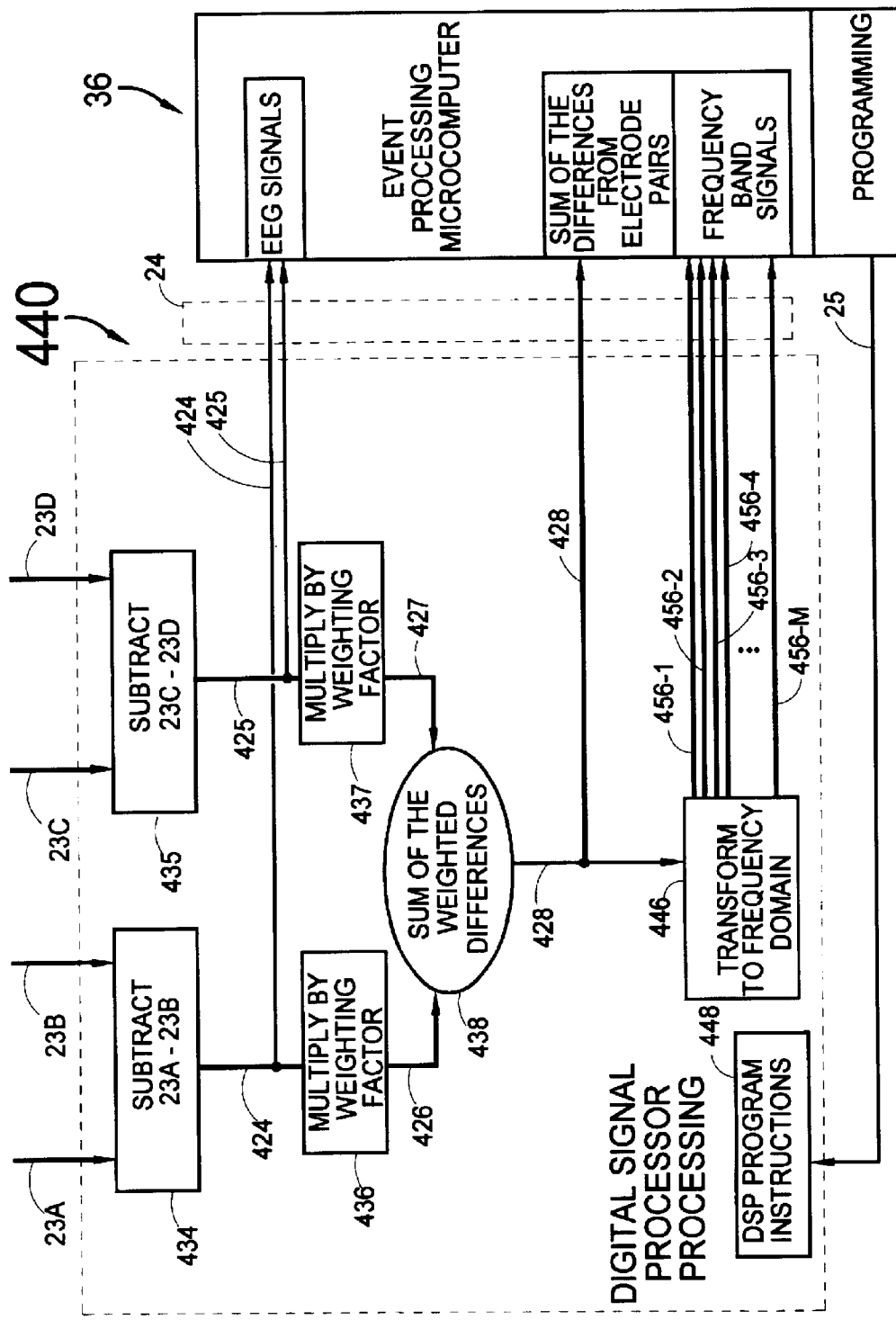
FIG. 6 illustrates a block diagram for an alternative algorithm for detection of a neurological event using the amplitude differences of signals from pairs of electrodes.

FIG. 6 shows an embodiment of the present invention in which the digital signal processor processing 440 based on DSP program instructions 448 takes the digitized EEG signals 23A, 23B, 23C and 23D from four brain electrodes 15A, 15B, 15C and 15D and creates the difference signal 424 from signals 23A and 23B using the subtraction algorithm 434, and the difference signal 425 from signals 23C and 23D using the subtraction algorithm 435. The difference signals 424 and 425 can then be multiplied by weighting factor algorithms 436 and 437 to adjust for difference in signal level for events arriving at each pair of electrodes. The resulting weighted differential EEG signals 426 and 427 are summed by the algorithm 438 to create the summed differential EEG signal 428. The summed differential EEG signal 428 can then be transformed into a set of frequency band signals 456-1 through 456-M by the algorithm 446 as previously described with respect to the digital signal processing 340 shown in FIG. 4.

The embodiment of FIG. 6 will work best when the electrode pairs 15A–15B and 15C–15D are located in positions that will cause the EEG signal differences 424 and 425 to be synchronized in time for EEG signals originating at the focus of a neurological event. It is also envisioned that a programmable delay adjustment, as described for FIG. 4, could be implemented here if the time delays for EEG signal differences 424 and 425 from a neurological event are not the same.

The summed differential EEG signal 428, the difference EEG signals 424 and 425, and the frequency band signals 456-1 through 456-M can be sent via interconnection 24 to the event processing microcomputer 36 for storage.

It is also envisioned that instead of digitizing the signal from each signal electrode 15A through 15N, with respect to a common electrode 16, the input stage could use any one or more pairs of brain electrodes with no single common electrode.

The processing 340 of FIG. 4 and 440 of FIG. 6 are examples of two different implementations of multiple step signal conditioning programs that can be run within the programmable digital signal processor 34 of FIGS. 2 and 3.

Figure 7:
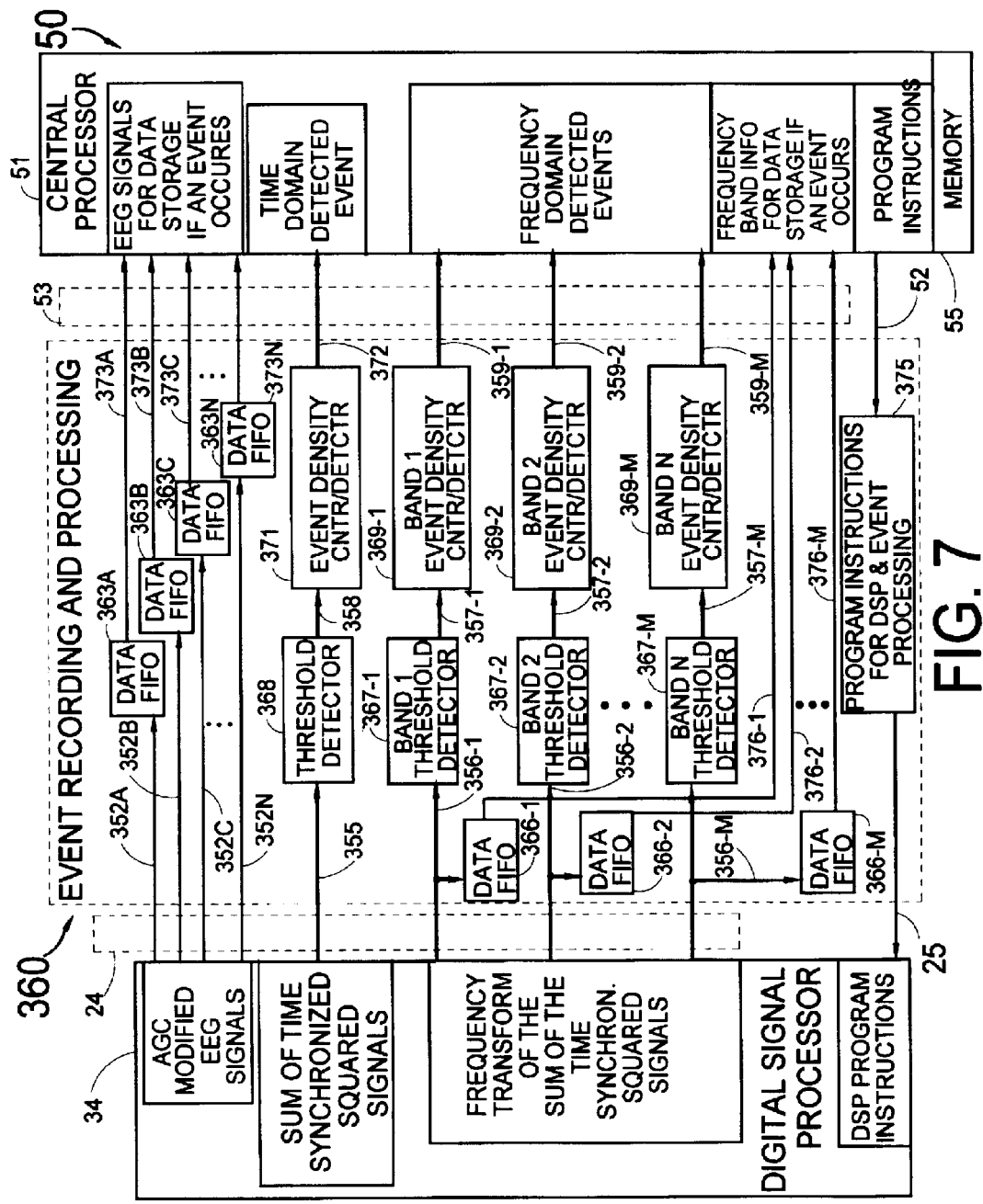
FIG. 7 is a flow chart of the event recording and processing which is carried on within the event processing microcomputer used for the second stage of an event detection sub-system.

FIG. 7 shows the software flow chart for event recording and processing 360 of the event processing microcomputer 36 used for the second stage of the event detection subsystem 30 shown in FIGS. 2 and 3. Specifically, event recording and processing 360 represents the algorithms and subroutines in software used by the event processing microcomputer 36 (hardware) as the event detection means and also to record relevant EEG and spectral band data. A primary objective of event recording and processing 360 software is to make possible the recording of AGC modified EEG signals 352A through 352N inclusive and the frequency band signals 356-1 to 356-M inclusive by the central processing system 50.

Figure 8:
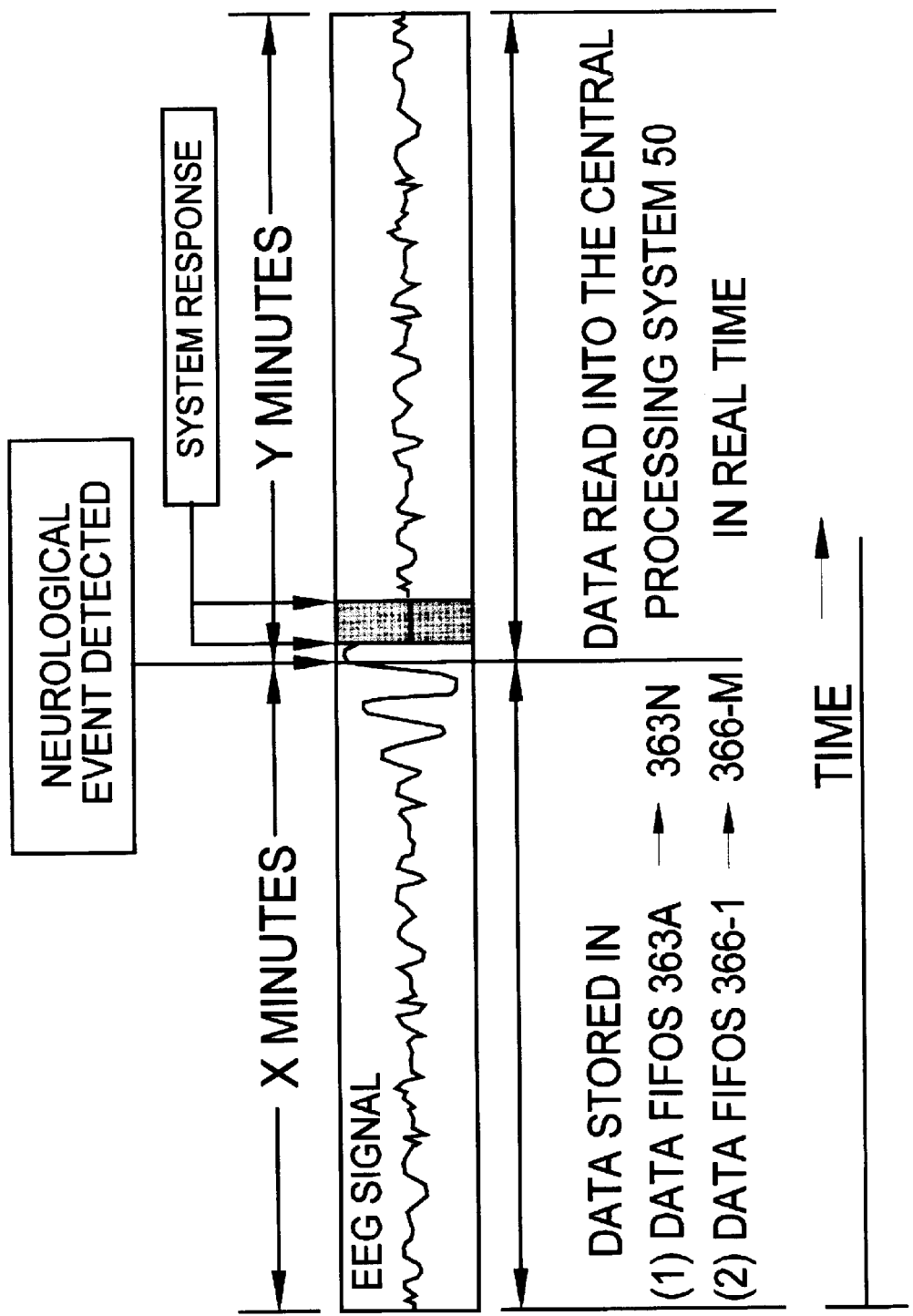
FIG. 8 illustrates the recording of EEG and/or EEG spectrum signals by the central processor.

FIG. 8 indicates that the central processing system 50 is capable of recording EEG and frequency band data for "X" minutes before a neurological event is detected and "Y" minutes after the neurological event is detected. The event recording and processing 360 of FIG. 7 is used to facilitate this data recording capability. Specifically, the EEG signals 352A through 352N (also see FIG. 4) are stored in data FIFO memories 363A through 363N. If an event is detected, the FIFOs 363A through 363N can be read by the central processor 51 via the link 53 to retrieve the stored EEG data streams 373A through 373N for a time "X" minutes before the event. The central processor 51 can also read the data FIFOs 363A through 363N in real time after detection of a neurological event for a period of "Y" minutes. Alternatively the data FIFOs 363A through 363N could be used to store and then read out "Y" minutes of data stored after the event is detected. In either case, the goal of retrieving "X" minutes of pre-event detection data and "Y" minutes of post-event detection data (as indicated in FIG. 8) can be achieved. It should be remembered that if there are N electrodes then there will be as many as N channels of AGC modified EEG data that can be recorded. However, the central processing system 50 may be programmed to record EEG data from a sub-set of the electrodes 15A through 15N (see FIG. 2). All data stored by the central processing system 50 can be retrieved by the patient's doctor for analysis with the goal of improving the response of the system 10 so as to more reliably stop a neurological event.

FIG. 7 also shows two different schemes for detecting an event. If the amplitude of the sum of the time-synchronized squared EEG signals 355 exceeds the event detection threshold 369 as shown in FIG. 5D (using threshold detector algorithm 368 of FIG. 7), the algorithm 368 sends a positive event detected message 358 to the event density counter/detector algorithm 371. The event density counter/detector algorithm 371 determines if there have been enough events in the most recent time period "T" to notify the central processor 51 with the event identified message 372 indicating that an event has really occurred. A typical time period "T" would be approximately 2 seconds but could be in the range from ½ to 100 seconds. The event density counter/detector algorithm 371 will reduce the number of false positive event identifications by eliminating short uncorrelated EEG bursts. If the number of events in the time period "T" is set equal to 1, then the system will be most sensitive and any time sample which exceeds the threshold 369 in the threshold detector algorithm 368, will be passed on as an event identified message 372. A typical setting for the number of events for a two second time period "T" would be four.

The system for detecting a neurological event based on the threshold detector 368 would involve processing data for the entire frequency spectrum of the sum of the time-synchronized and squared EEG signals 355. As shown in FIG. 4 the signal 355 can be transformed into a set of frequency band signals 356-1 through 356-M inclusive each of which signals is of limited bandwidth as compared with the broadband signal 355. Each of the frequency band signals 356-1 through 356-M of FIG. 7 can be analyzed by a corresponding threshold detector algorithm 367-1 through 367-M, respectively, in a manner exactly analogous to the threshold detector algorithm 368 used to detect events from the broadband signal 355.

In a manner analogous to the threshold detector algorithm 368, each of the set of threshold detector algorithms 367-1 through 367-M can send a positive event detected signal 357-1 through 357-M to a corresponding frequency band event density counter/detector 369-1 through 369-M when the amplitude of the frequency band signal 356-1 through 356-M exceeds a preset threshold level. The frequency band event density counter/detectors 369-1 through 369-M will, analogous to the event density counter/detector 371, determine if there are a sufficient number of events per time period "T" in any of the bands 1 through M to send an event identified message 359-1 through 359-M to the central processor 51 indicating that a neurological event has occurred.

Analogous to the storage of the AGC modified EEG signals 352A through 352N by the data FIFOs 363A through 363N, each of the M frequency band signals 356-1 through 356-M is stored in FIFO memories 366-1 through 366-M, so that if an event is detected, the FIFOs can be read by the central processing system 50 via the link 53 to retrieve the frequency band data streams 376-1 through 376-M for a time "X" before event detection until some time "Y" after event detection. As previously described, FIG. 8 illustrates this concept for data storage.

Constructing computer code to store and retrieve sampled digital signals from FIFO memory is well known in the art of software design. Comparing an input signal amplitude against a preset threshold, determining the number of counts per unit time and comparing the counts per unit time against a preset number of counts per unit time are also well known in the art of software design.

It should be understood that the software which is the digital signal processor processing 340 (see FIG. 4) is run by the programmable digital signal processor 34 according to the DSP program instructions 348. In a similar manner, the software for event recording and processing 360 (see FIG. 7)

is run by the event processing microcomputer 36 of FIG. 4 according to the program instructions for DSP and event processing 375. Additionally the programming instructions for DSP and event processing 375 serves as a pass through for the DSP program instructions 348 of FIG. 4. The program instructions for DSP and event processing 375 are received by the event processing microcomputer 36 (using the software for event recording and processing 360) from the central processor 51 via the interconnection 52. The DSP program instructions 348 (see FIG. 4) are received over interconnection 25 by the digital signal processor 34 from the program instructions for DSP processing and event processing 375 of FIG. 7.

The thresholds to be used for detection by the threshold detector algorithms 368 and 367-1 through 367-M and the required event densities for event identification by the event density counter/detector algorithms 371 and 369-1 through 369-M, will typically be programmed to minimize the chance of missing a "real" neurological event even though this could result in the occasional false positive identification of an event. This bias toward allowing false positives might typically be set to produce from ½ to 5 times as many false positives as "real" events.

It Is also envisioned that the software for event recording and processing 360 might not require a separate microcomputer but could operate either as a set of subroutines in the central processor 51 or a set of subroutines in the programmable digital signal processor 34.

It is also envisioned that the event recording and processing software 360 could be programmed to provide an event detection means based on detecting specific aspects of the waveform of either time or frequency domain outputs of the signal conditioning by the digital signal processor 36. Such aspects of the waveform could include pulse width, first derivative or waveform shape.

Figure 9:
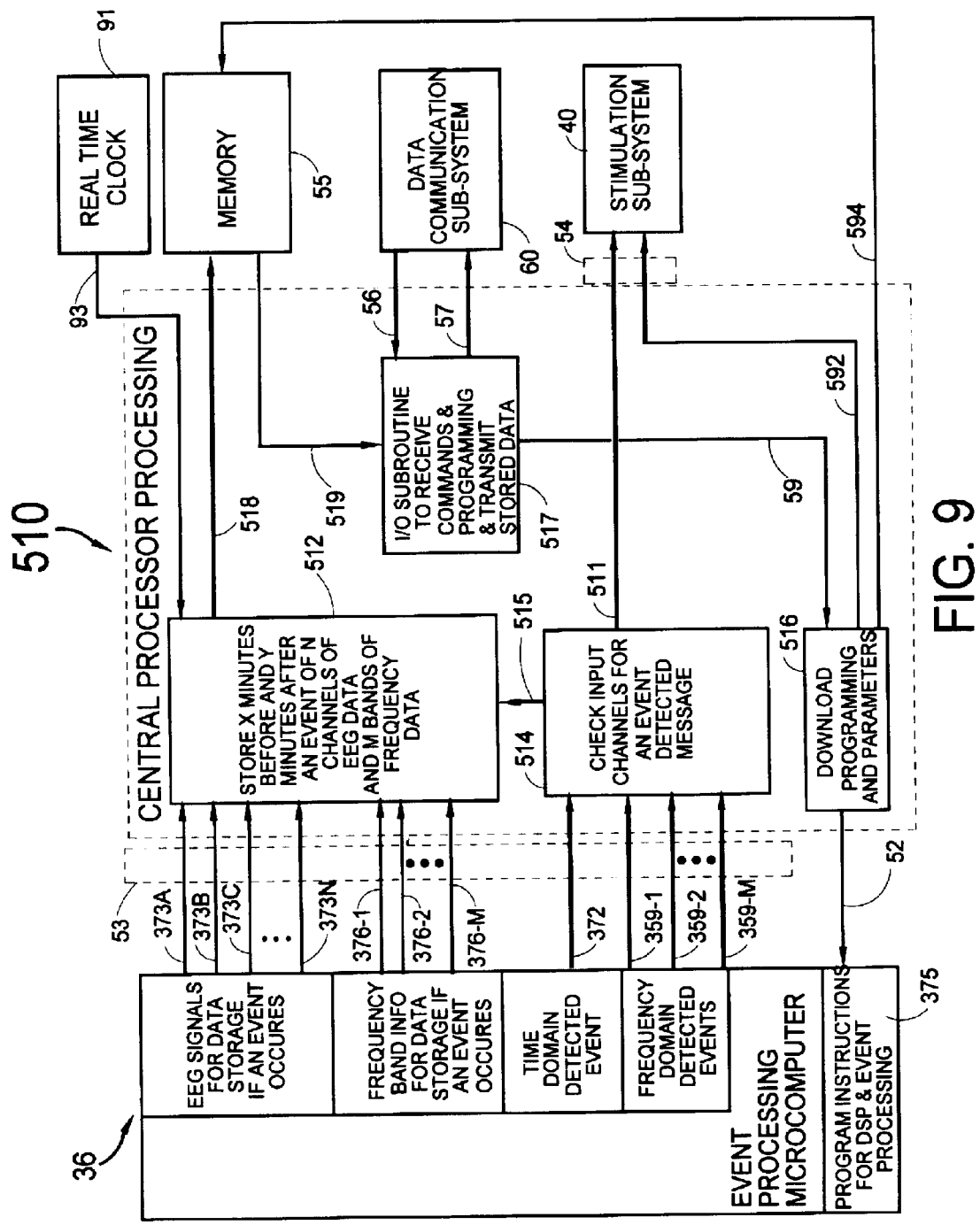
FIG. 9 shows a flow chart of the central processor function for: (1) receiving event detection information from the event detection sub-system; (2) sending delay and threshold parameters to the event processing microcomputer and digital signal processor; (3) storing event related data; (4) inducing responsive brain stimulation through the stimulation sub-system; and (5) communicating externally for physician data read out and system programming.

FIG. 9 shows a flow chart of the software for central processor processing 510 as run by the central processor 51 of FIG. 2. The central processor 51 receives event detection messages 372 and 359-1 through 359-M, EEG data streams 373A through 373N and the frequency band data streams 376-1 through 376-M from the event processing microcomputer 36. The central processor 51 of FIG. 2 also sends and receives data to and from the data communication sub-system 60 via interconnections 56 and 57. The processing 510 processes these messages, signals, and data streams.

Algorithm 514 receives the event detection messages 372 and 359-1 through 359-M provided by the event processing microcomputer 36 via the link 53. When the algorithm 514 receives such a message indicating that a neurological event has occurred, the algorithm 514 calls the subroutine 512. The calling of the subroutine 512 by the algorithm 514 is indicated by the element 515. The subroutine 512 reads and saves to the central processor's memory 55 via the link 518, the last X minutes of stored EEG data streams 373A through 373N and frequency band data streams 376-1 through 376-M from the event processing microcomputer 36. The algorithm 512 will continue to read and save to the central processor's memory 55, the next "Y" minutes of EEG data streams 373A through 373N and frequency band data streams 376-1 through 376-M from the event processing microcomputer 36. As seen in FIG. 8, these data streams may include a blank period during stimulation followed by data that can be analyzed to determine the efficacy of the treatment. The algorithm 514 also causes a signal 511 to be sent to the stimulation sub-system 40 via the link 54 to cause the stimulation sub-system 40 to respond as programmed to stop the neurological event.

Values for X and Y will typically be several minutes for X and as much as a half-hour for Y. The memory 55 must be large enough for at least one event and could be large enough to hold 10 or more events. The values X and Y like other parameters are programmable and adaptable to the needs of each particular patient.

Figure 11:
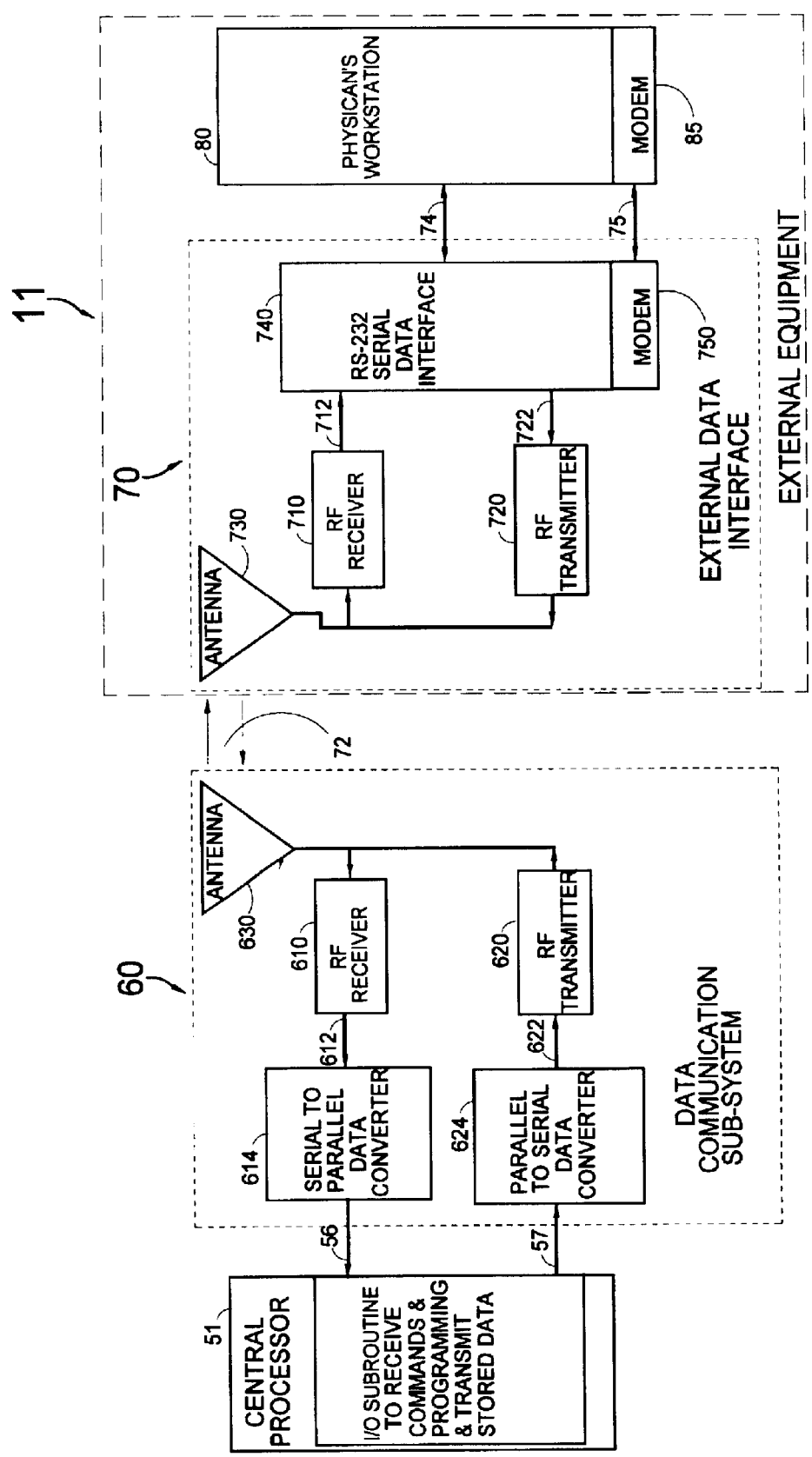
FIG. 11 is a block diagram of the data communication sub-system and external data interface.

The I/O subroutine 517 receives physician commands from the data communication sub-system 60 via the link 56 and, in turn, reads and sends back via the link 57 the data stream 519 containing the event related data previously stored in the memory 55 by the algorithm 512. These data are transmitted to the external equipment 11 by the data communication sub-system 60 via the wireless link 72 as shown in FIGS. 2 and 11.

The I/O subroutine 517 also plays a key role in the downloading of software programs and parameters 59 to the programmable sub-systems of the implantable system 10 of FIG. 2. These programmable sub-systems include the event detection sub-system 30, the central processing system 50 and the stimulation sub-system 40. The programmable components of the event detection sub-system 30 are the programmable digital signal processor 34 and the event processing microcomputer 36 shown in FIG. 3. The programming instructions and parameters 59 for the programmable sub-systems 30, 40 and 50 are downloaded through the I/O subroutine 517 by the programming and parameters downloading subroutine 516 of the central processor processing 510. The subroutine 516 stores the instructions and parameters 59 and downloads the program instructions for DSP and event processing 375 (also see FIG. 7) for the event detection sub-system 30 via link 52 to the event processing microcomputer 36. The subroutine 516 also downloads the stimulation sub-system instructions and parameters 592 via the link 54 to the stimulation sub-system 40. The subroutine 516 also updates the memory 55 with the programming instructions and parameters 594 for the central processor processing 510.

Programmable microprocessors or self-contained microcomputers, such as the Intel 8048 and 8051, which contain read only memory for basic programs and random access memory for data storage and/or program storage, can be used to implement the central processor processing 510 as previously described. It is also envisioned that a custom VLSI chip involving microprocessor, signaling and memory modules could be produced specifically for this application. All of the previously described algorithms to store data, send notification signals and messages and make decisions based on input data are straightforward for a software programmer to implement based on the current state of the art.

It is also clear that current memory technology should be suitable for EEG storage. For example, the EEG storage for a 4 electrode system using 8 bits (one byte) per sample at a sampling rate of 250 samples per second (required for frequencies up to 125 Hz) will require 60,000 bytes per minute of data storage. Having 100 minutes of storage would require only 6 megabytes, which is readily achievable using current memory chip technology. Thus if both X and Y were each 1 minute, then a total of 50 neurological events could be stored in the 6 megabyte memory.

It is also envisioned that with well-known data compression techniques such as adaptive pulse code modulation, the memory requirements can be reduced significantly.

It should be understood that instead of using random access memory to store the EEG data, non-volatile memory such as "flash memory" could be used to conserve power.

Figure 10:
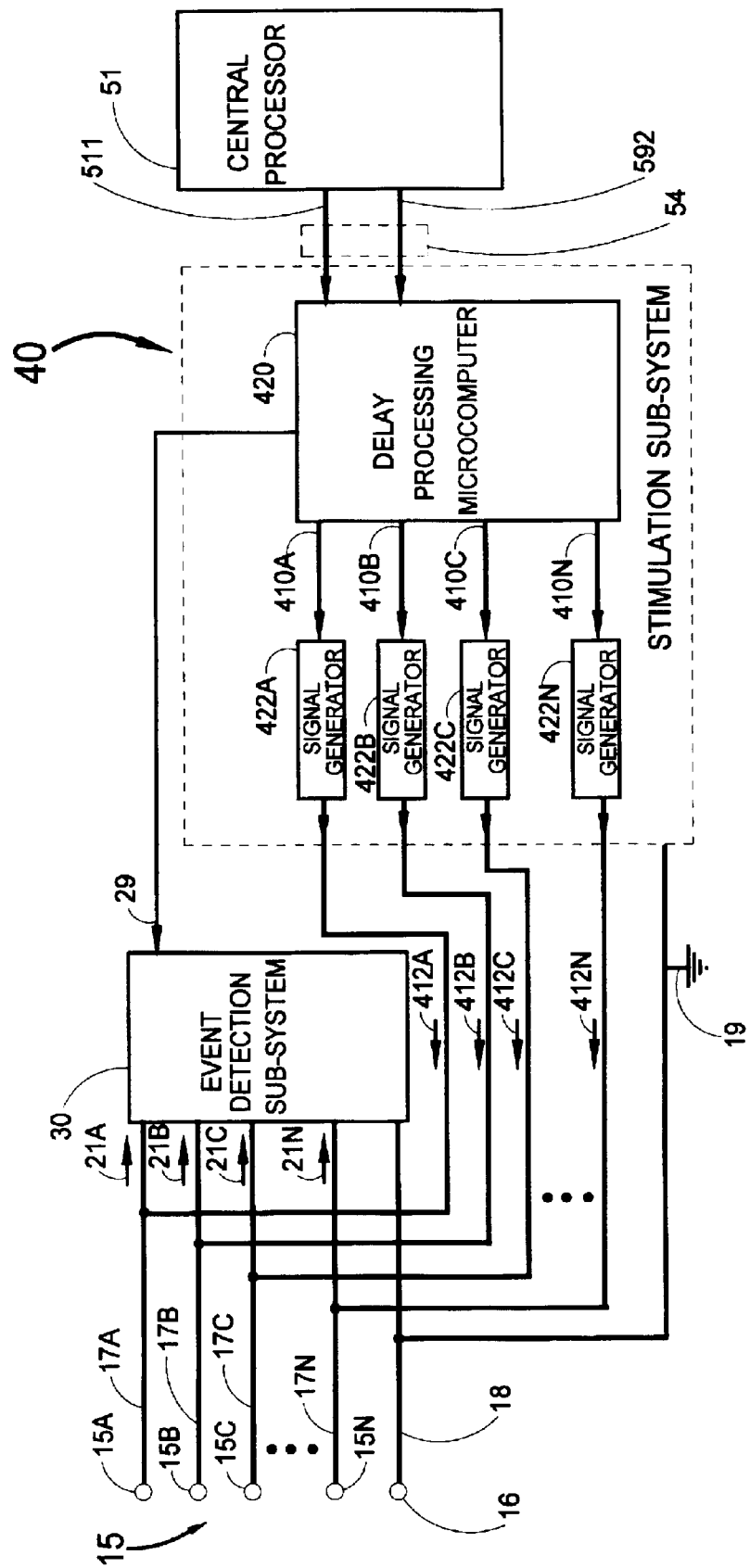
FIG. 10 is a block diagram of the stimulation sub-system as used to stimulate the brain responsive to a detected event.

FIG. 10 illustrates the stimulation sub-system 40 including its interconnections to other sub-systems. The stimulation sub-system 40 is used to stimulate the brain, responsive to a detected event. The preferred embodiment of the stimulation sub-system 40 comprises a delay processing microcomputer 420 and N signal generators 422A through 422N attached to the electrodes 15A through 15N by the wires 17A through 17N. The event detection signal 511 from the central processor 51 is received by the delay processing microcomputer 420, which first sends a signal via the link 29 to the event detection sub-system 30 to shut down event detection during stimulation. The delay processing microcomputer 420 will then feed stimulation command signals 410A through 410N to the signal generators 422A through 422N for a specific pre-programmed time period. The stimulation command signals 410A through 410N may be simultaneous or may have a relative delay with respect to each other. These delays can be downloaded by the instruction and parameter download 592 from the central processor 51 via the link 54. It may be desirable that the delays be adjusted so that the stimulation signals 412A through 412N from the signal generators 422A through 422N reach the neurological event focus in the brain at the same time and in-phase. This could enhance performance of the stimulation sub-system 40 in turning off a neurological event. Alternately, experience may indicate that certain signals being out of phase when they arrive at the neurological event focus may be particularly efficacious in aborting a neurological event.

The stimulation command signals 410A through 410N can be used to control the amplitude, waveform, frequency, phase, and time duration of the signal generators' output signals.

The typical stimulation signals 412A through 412N generated by the signal generators 422A through 422N should be biphasic (that is with equal energy positive and negative of ground) with a typical frequency of between 30 and 200 Hz, although frequencies of between 0.1 and 1000 Hz may be effective. It is also envisioned that pure d-c voltages might be used, although they are less desirable. If frequencies above 30 Hz are used, the signal generators could be capacitively coupled to the wires 17A through 17N. The typical width of the biphasic pulse should be between 250 and 500 microseconds, although pulse widths of 10 microseconds to 10 seconds may be effective for a particular patient. Typical voltages applied may be between 1 millivolt and 10 volts rms. The stimulation would typically be turned on for several seconds although times as short as a 1 millisecond or as long as 30 minutes may be used.

Biphasic voltage generation circuits are well known in the art of circuit design and need not be diagrammed here. Similarly, the code to cause the delay processing microcomputer 420 to provide different command parameters to the signal generators 422A through 422N is easily accomplished using well known programming techniques.

Although the delay processing microcomputer 420 is shown here as a separate unit, it may be practical to have the central processor 51 or the event detection microcomputer 36 of FIG. 3 provide the required processing. Consolidating many of the processing functions within a single processor is practical with the system 10 of FIG. 2 as the real time demands on any one system typically occurs when the others are not extremely busy. For example, during processing to identify an event, there is no need for data I/O, EEG storage or stimulation. When an event is detected and there is a need for EEG storage and stimulation, there is reduced need for event detection processing.

It is also envisioned that the stimulation sub-system 40 could operate with only one electrode such as a single electrode centrally located at an epileptic focus, or a deep electrode implanted in the thalamus or the hippocampus of the brain. If this were the case, the delay processing microcomputer 420 would not be needed, and only a single signal generator circuit would be required. By "located at an epileptic focus" it is meant that the electrode would be placed within 2 centimeters of the center of that focus.

FIG. 11 shows the block diagram of the data communication sub-system 60 and the external data interface 70 including interconnections to the central processor 51 and the physician's workstation 80. When communication from the physician's workstation 80 to the central processor 51 is desired, the antenna 730 of the external data interface is placed near the antenna 630 of the data communication sub-system 60. The workstation 80 is then connected by the cable 74 to an RS-232 serial data interface circuit 740 of the external data interface 70. The RS-232 serial data interface circuit 740 connects to the RF transmitter 720 and RF receiver 710 through the serial connections 722 and 712, respectively. Alternatively, if the patient is remotely located from the physician's workstation 80, the workstation 80 can be connected to the RS-232 serial data interface over a dial-up connection 75 using the modems 750 and 85.

Once the connection 74 or 75 has been established, wireless signals 72 can sent to and from the RF transmitter/receiver pair 610 and 620 of the data communication sub-system 60 and the RF transmitter/receiver pair 710 and 720 of the external data interface 70. The wireless signals 72 are used to command software updates via the link 612 through the serial-to-parallel data converter 614 and the link 56 to the central processor 51. The wireless signals 72 are also used to send stored data back through the link 57 through the parallel-to-serial data converter 624 through the link 622 to the RF transmitter 620.

RF transceiver circuitry and antennas similar to this are used in data communication with heart pacemakers and defibrillators, and therefore, this technology is well known in the art of implantable programmable devices. RS-232 interfaces, serial to parallel and parallel to serial conversion circuits, are also well known.

Figure 12:
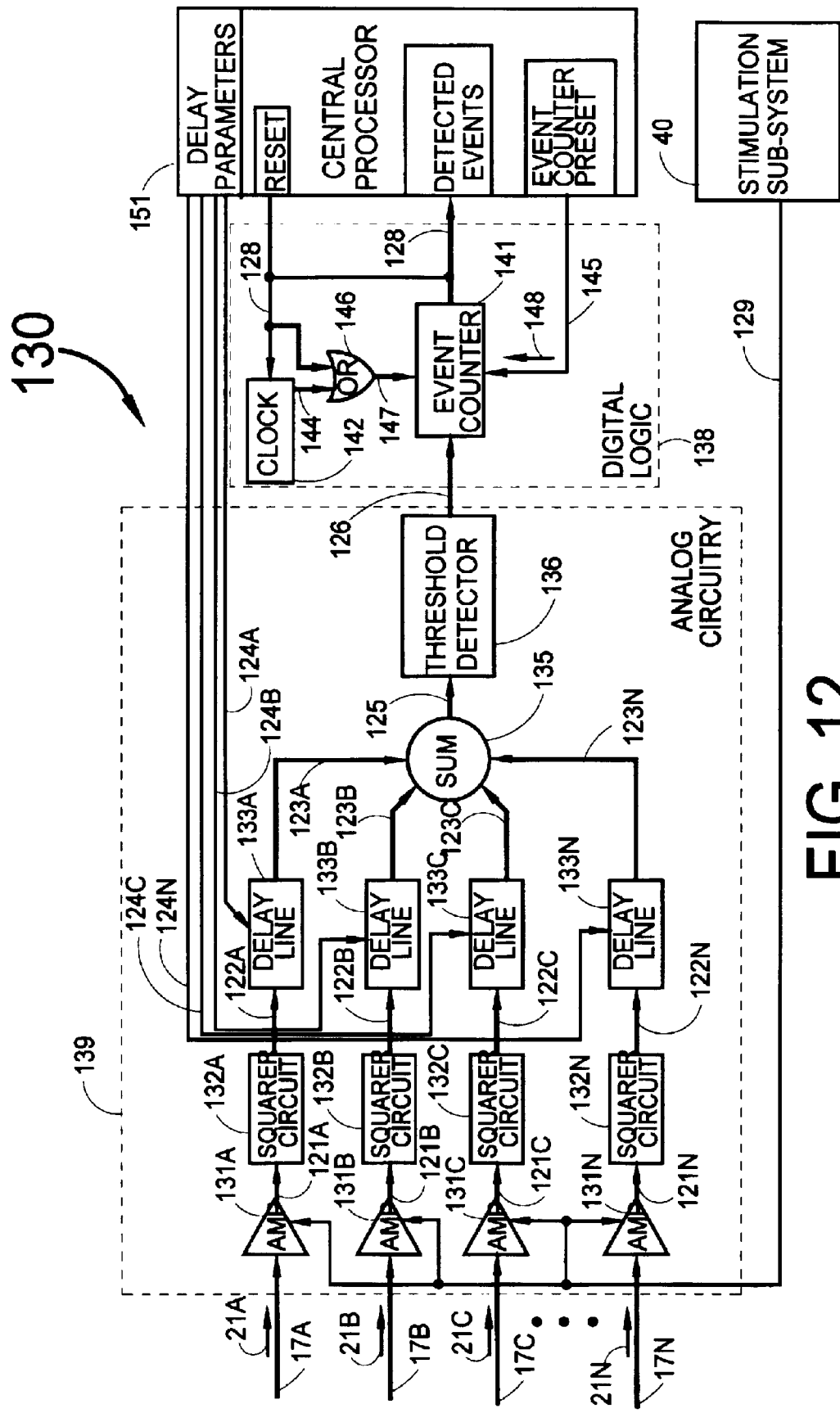
FIG. 12 is a block diagram of a hybrid analog/digital representation of the event detection sub-system using time domain information for event detection.

FIG. 12 is a block diagram of a hybrid analog/digital embodiment of an event detection sub-system 130 that uses time domain information for event detection. In this embodiment, analog circuitry 139 is used to process and detect possible neurological events, and digital logic circuitry 138 is used to check if the density of possible events is sufficient to declare a "real" event. As in FIG. 3, the incoming EEG signals 21A through 21N on wires 17A through 17N are amplified by the amplifiers 131A through 131N which may also provide band-pass or low-pass filtering and/or AGC of the signals 21A through 21N resulting in the amplified signals 121A through 121N which are then squared by the squarer circuits 132A through 132N resulting in the squared signals 122A through 122N. The squared signals 122A through 122N are then processed by a series of analog delay line circuits 133A through 133N to create the squared and time-synchronized EEG signals 123A through 123N, which are subsequently added together by the summing circuit 135. The resulting summed time-synchronized signal 125 is then fed into a threshold detection circuit 136 which will output a digital pulse 126 whenever the summed time-synchronized signal 125 exceeds a pre-set threshold. The digital pulses 126 collected over time are then processed by the digital logic circuit 138 to determine if the event is real or not. The delay parameters 124A through 124N are input to the delay lines 133A through 133N from the central processor 151 and can be pre-set for a particular patient.

Setting the values for these time delays could be based on measured delays of EEG signals received from an epileptic focus during diagnostic testing of the patient using the implanted system 10 of FIG. 2. During brain stimulation, a signal 129 is sent from the stimulation sub-system 40 to shut down the amplifiers 131A through 131N to avoid amplifier overload or mistakenly identifying a stimulation signal as a neurological event signal.

Analog integrated circuits to multiply or sum analog signals are commercially available. Integrated circuit bucket brigade analog delay lines are also commercially available. It is also envisioned that a hybrid circuit containing multipliers, summers and delay lines could be produced to miniaturize the system 130. A standard comparator circuit, also available as an integrated circuit, can be used as the threshold detector 136 to compare the signal 125 with a pre-set threshold. If the threshold is exceeded, then a pulse is sent via the connection 126 from the threshold detector circuit 136 to the event counter 141 of the digital logic 138.

The digital logic 138, which counts the number of event pulses per second emitted by the threshold detector 136, can be implemented using a simple programmable microcomputer similar to that described for event recording and processing 360 shown in FIG. 7, or it can be implemented by a collection of standard digital logic and counting circuitry. Such a set of circuitry could use a counter 141 to count the possible event pulses 126 generated by the threshold detector 136. An event detected pulse 128 would be emitted by the counter 141 only when it overflows. If the counter 141 is reset once a second by a reset pulse 147 from an OR gate 146 which has been sent a pulse 144 from the clock 142, then only if the counter 141 overflows in the one second time period between reset pulses 147 will the event detected pulse 128 be generated. Certain available counter chips can be reset to a preset number rather than 0. In FIG. 12, the event counter 141 could be implemented with such a counter chip so that a reset signal will cause the counter to reset to a preset number 148 that would be set via the connection 145 from the central processor 151. Thus, for example, an 8 bit counter (which counts up to the number 256) could be set to overflow when the number of pulses counted by the counter 141 causes it to count from the downloaded preset number 148 to the number two hundred and fifty-six in less than one second. Of course, times of less than 1 second or more than 1 second can also be used for the time between the pulses 144 from the reset clock 142. The event detected pulse 128 is also used to reset both the clock 142 and the event counter 141. An OR gate 146 will allow the event counter 141 to be reset by either the pulse 144 from the clock 142 or the event detected pulse 128. The processing by the central processor 151 would be analogous to that shown in FIG. 9.

The specific threshold to be used for detection by the threshold detector 136 and the preset 148 for the event counter 141 will typically be set to minimize the chance of missing a "real" event even though this will result in occasional false positive identification of an event.

Figure 13:
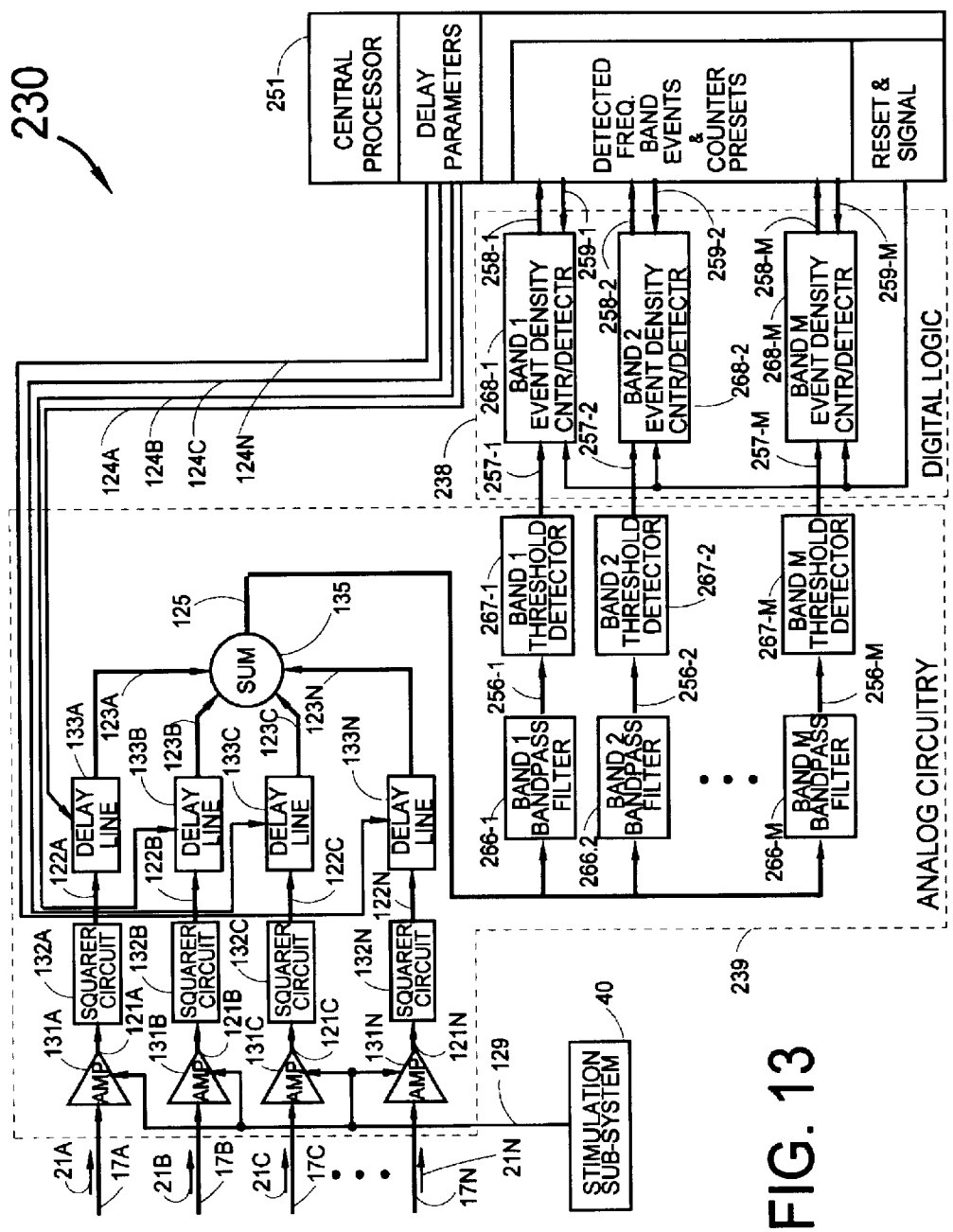
FIG. 13 is a block diagram of a hybrid analog/digital representation of the event detection sub-system using frequency domain information for event detection.

FIG. 13 is a block diagram of a hybrid analog/digital representation of still another embodiment of the event detection sub-system 230 using frequency domain information for event detection. In this embodiment, analog circuitry 239 is used to process and detect possible events in each of M frequency bands. Digital logic circuitry 238 is used to check if the density of possible events is sufficient to declare a "real" event. The front end (up through and including the sum 135) of the analog circuitry 239 of the sub-system 230 is identical to the front end of the analog circuitry 139 of FIG. 12. As in FIG. 12, the incoming EEG signals 21A through 21N on wires 17A through 17N are amplified by the amplifiers 131A through 131N. These amplifiers 131A through 131N (which may also provide band-pass or low-pass filtering of the signals 21A through 21N) produce the amplified signals 121A through 121N. The amplified signals 121A through 121N are then squared by the squarer circuits 132A through 132N resulting in the squared signals 122A through 122N. The squared signals 122A through 122N are then processed by a series of analog delay line circuits 133A through 133N to create the squared and time-synchronized EEG signals 123A through 123N, which are subsequently added together by the summing circuit 135. The resulting summed time-synchronized signal 125 is fed to a set of analog band-pass filters 266-1 through 266-M for the M frequency bands. The resulting band signals 256-1 through 256-M are examined by the threshold detectors 267-1 through 267-M analogous to the threshold detector 136 of FIG. 12. Each of the threshold detectors (267-1 through 267-M) will generate a corresponding pulse (257-1 through 257-M) when a preset threshold is exceeded analogous to the pulse 126 generated by the threshold detector 136 of FIG. 12. The pulses 257-1 through 257-M are fed into the event density counter/detectors 268-1 through 268-M each identical to the digital logic circuit 138 of FIG. 12. The event density counter/detectors 268-1 through 268-M will feed the detected frequency band event pulses 258-1 through 258-M to the central processor 251.

The central processor 251 processes events from event density counter/detectors in a similar manner to the central processor 151 of FIG. 12. The main differences are that the counter presets 259-1 through 259-M may be different for each of the bands as required to optimize sensitivity. During responsive brain stimulation, a signal 129 is sent from the stimulation sub-system 40 to shut down the amplifiers 131A through 131N to avoid amplifier overload or mistakenly identify a stimulation signal as an event signal. The processing by the central processor 251 would be analogous to that shown in FIG. 9.

Figure 14:
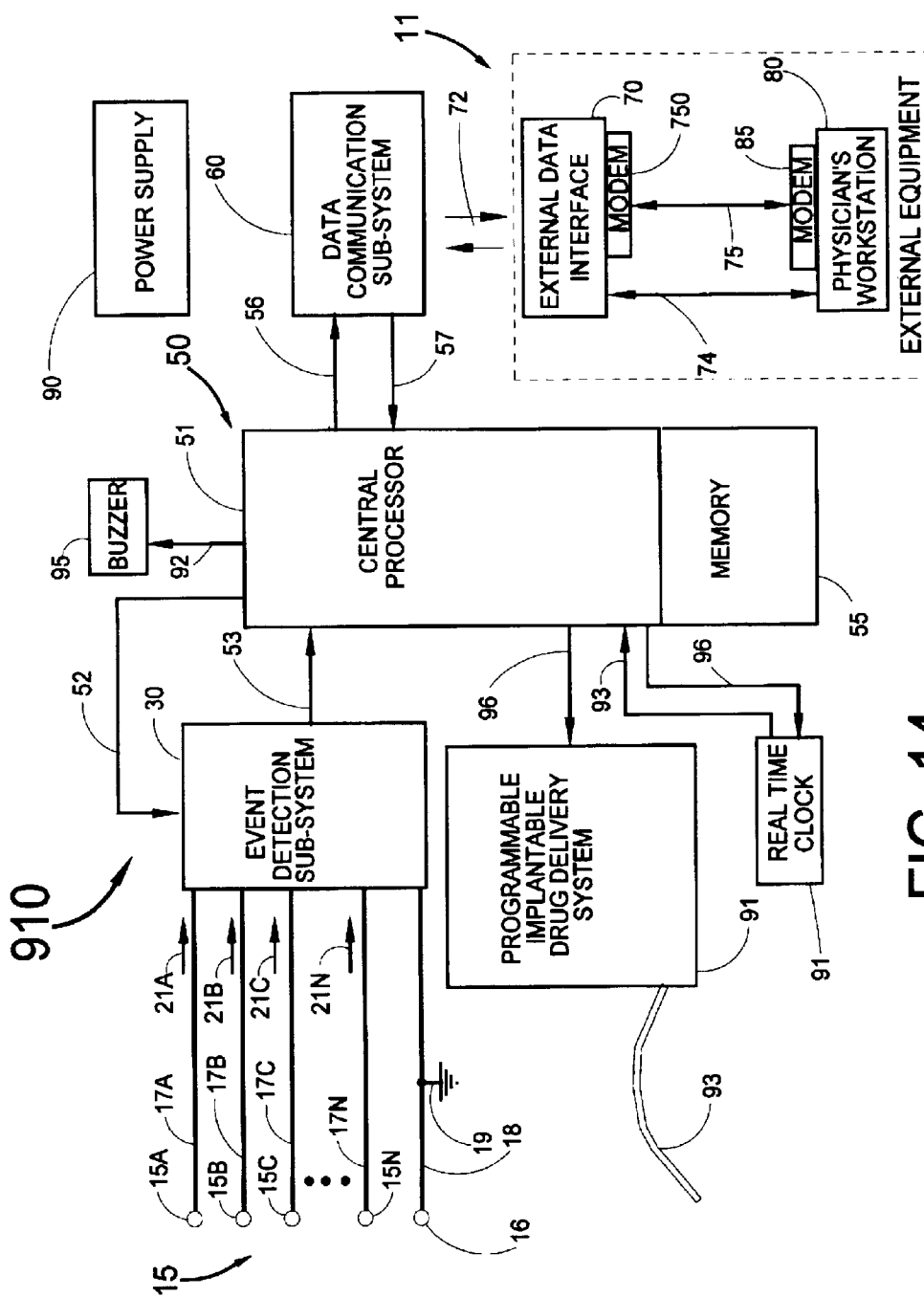
FIG. 14 is a block diagram of an implantable system that can respond to a detected neurological event by infusing medication into the patient's body.

FIG. 14 is a diagram of an implantable system 910 which can respond to a detected neurological event by infusing medication from an implantable medication system 91 into the patient's body through the hollow catheter 93. The system 910 is identical to the system 10 of FIG. 2 except that the programmable drug delivery sub-system 91 replaces the stimulation sub-system 40 of FIG. 2 as the subsystem that provides the response to an neurological event detected by the event detection sub-system 30. In this embodiment, the signal indicating that an event has been detected and the programming instructions for the implantable drug delivery system 91 are transmitted via the link 96 from the central processor 51. It may be desirable to place the outlet of the catheter 93 into the cerebrospinal fluid (CSF) to provide rapid infusion to all areas of the brain, or it may be desired to have the outlet of the catheter 93 positioned to deliver medication to one specific location in the brain or possibly into the bloodstream.

The operation of the system 910 of FIG. 14 for detecting and treating a neurological event such as an epileptic seizure is as follows:

1. The event detection sub-system 30 continuously processes the EEG signals 21A through 21N carried by the wires 17A through 17N from the N electrodes 15A through 15N.
2. When an event is detected, the event detection subsystem 30 notifies the central processor 51 via the link 53 that an event has occurred.

3. The central processor 51 signals the drug delivery system 91 via the link 96 to infuse medication through the catheter 93 into the patient's body as a means for stopping a neurological event.
4. The drug delivery system 91 delivers pre-programmed drug infusion to the desired site.
5. The central processor 51 will store EEG and event related data from X minutes before the event to Y minutes after the event for later analysis by the patient's physician.
6. The central processor 51 may initiate a "buzz" to notify the patient that an event has occurred by sending a signal via the link 92 to the buzzer 95.

Programmable implantable drug delivery systems are described in some detail in the Fischell patent U.S. Pat. No. 4,373,527. It is also envisioned that both electrical stimulation and drug delivery could be used together to improve the outcome in the treatment of a neurological disorder.

It should also be understood that although the invention described herein has been described with analog or digital implementations of various aspects of the invention, the invention may combine analog and digital elements described herein in different combinations than as described.

In addition, although the previous descriptions relate to a fully implantable system, an externally worn system with implanted electrodes could function adequately and would allow a plug-in interface to the data communication subsystem 60 and simple battery replacement. It is also envisioned that the techniques described above would work with an external device with electrodes attached to the outside of the head. External devices would have great merit in determining if an implantable system would work well enough to be warranted. An external version with implanted electrodes could be used to record EEG signals from neurological events to calculate the optimal programming algorithms and parameters to be used by a permanently implanted system using the same set of electrodes.

It is also envisioned that the EEG recording capabilities of the present invention could be used without the event detection and stimulation components to store patient EEG activity for diagnostic purposes.

Figure 15:
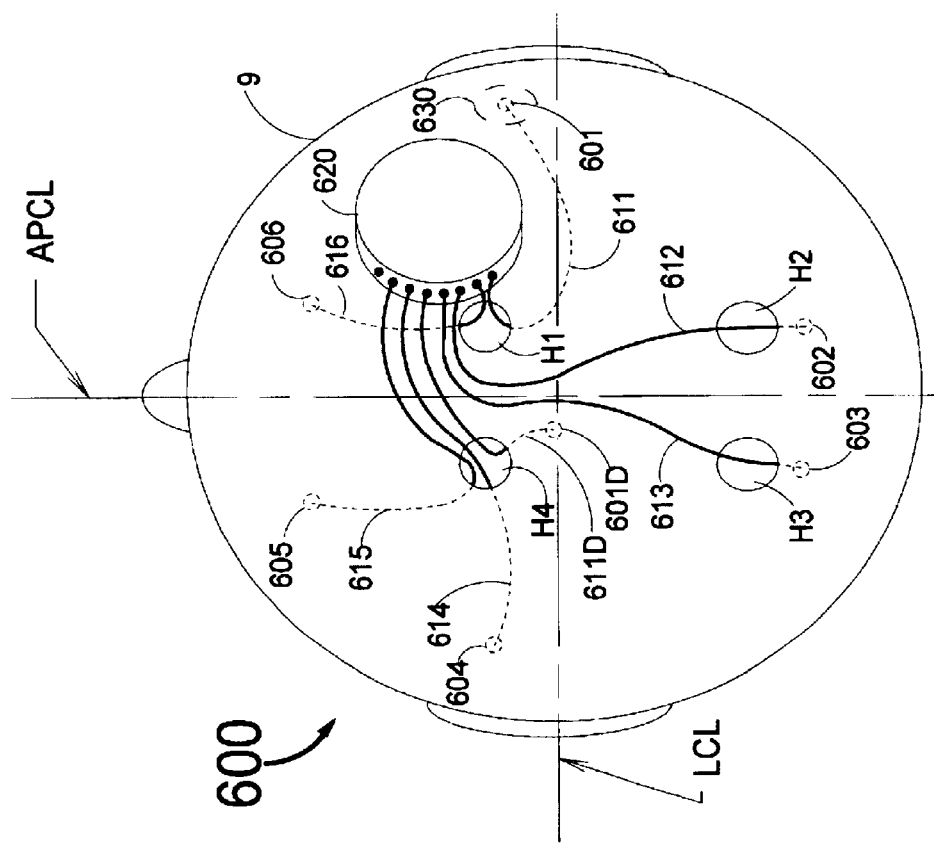
FIG. 15 is a top view of a human head showing the arrangement of a multiplicity of electrodes connected by wires to a control module that is implanted within the cranium.

Novel arrangements for the physical placement of the various parts of a system for the treatment of neurological disorders are shown in FIGS. 15 to 25 inclusive. Specifically, FIG. 15 shows a top view of an intracranial system 600 consisting of brain surface electrodes 601, 602, 603, 604, 605 and 606 connected by wires 611, 612, 613, 614, 615 and 616 respectively which provide an electrical conducting means to join the electrodes 601 through 606 to a control module 620. Thus the proximal end of each of the wires 611 through 616 is connected to the control module 620, and the distal end of each of the wires 611 through 616 is connected to an electrode. Inside the patient's head 9, these surface electrodes 601–606 are placed between the bottom of the cranium (i.e., inside the skull) and the top of the dura mater that surrounds the brain. Thus this is an epidural placement of the surface electrodes. Although six surface electrodes are shown in FIG. 15, it is envisioned that as many as 12 or more active electrodes could be usefully implanted. It is further envisioned that the metal case of the control module 620 could serve as a common or indifferent electrode that also could be considered to be at ground potential. It is further envisioned that the control module might utilize a case that is non-conducting in which only part of the outer surface is conducting so as to provide one or more electrodes. Also shown in FIG. 15 is a deep electrode 601D connected by wire 611D to the control module 620. It is anticipated that as many as eight deep electrodes could be used with the intracranial system 600. One or more deep electrodes might advantageously be placed in the hippocampus and/or the thalamus or possibly some other portion of deep brain tissue.

Figure 16:
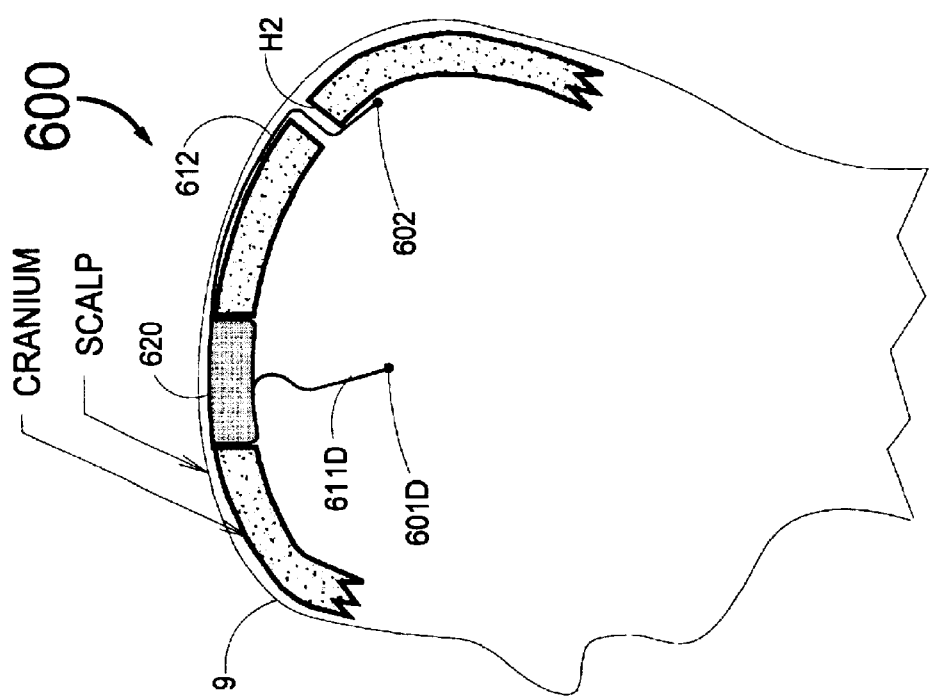
FIG. 16 is a side view of a human head showing the arrangement of one surface and one deep electrode connected by wires that pass through a hole in the cranium and connect to a control module that is implanted within the cranium.

FIG. 16 is a simplified side view of the human head 9 into which the intracranial system 600 has been implanted. In this simplified view, only one brain surface electrode 602 is shown and one deep electrode 601D. The brain surface electrode 602 is connected by the insulated wire 612 to control module 620. Also shown in FIG. 16 is the deep electrode 601D connected by the wire 611D to the control module 620.

FIGS. 15 and 16 also show that the control module 620 is located in an anterior portion of the patient's head 9. By an anterior portion is meant that it is located anterior to the head's lateral centerline (LCL) that roughly goes through the center of the ears. Furthermore, the control module 620 cannot be situated on the anterior-posterior centerline (APCL) because just under the APCL is the very large sagittal sinus vein, and it would be inadvisable to place the control module 620 at such a location. The reason for placing the control module 620 in the anterior half of the patient's cranium is that the middle meningeal artery and its branches, (which arteries all lie posterior to the LCL) cause grooves to be formed in the underside of the cranium. Therefore, that location is also inappropriate for removing the considerable volume of cranium bone that should be removed for placement of the control module 620.

FIGS. 15 and 16 also show that the electrodes are connected by wires to the control module 620 via holes that are made by removing bone from the patient's cranium. Specifically, the interconnecting wires 611, 612, 613 and 614 pass respectively through the holes H1, H2, H3 and H4. It can also be seen in FIG. 15 that the wire 616 passes through the hole H1 and wires 615 and 611D pass through the hole H4. The reason for this method of sometimes running most of the wire length between the scalp and the cranium and at other times running most of the wire length between the bottom of the cranium and the dura mater has to do with the movement of the scalp relative to the cranium which occurs on the anterior portion of the patient's head and also is done to avoid placing the wires epidurally where the middle meningeal artery and its branches have made grooves in the interior surface of the cranium. Specifically, it will be noted that the wires 612 and 613 are placed under the scalp for most of their length because in this posterior portion of the patient's head the scalp exhibits very little motion relative to the cranium but the middle meningeal artery and its branches do cause interior surface grooves in the cranium in this posterior region of the head. The reverse situation is seen for the connecting wires 615 and 616. In this case, because there is considerable motion of the scalp relative to the cranium in the anterior portion of the patient's head, most of the length of the wires 615 and 616 is placed epidurally where there are no grooves in the interior surface of the cranium.

Indicated by phantom lines in FIG. 15 is the location of an epileptic focus 630 where an electrode 601 has been placed. As previously described, it may be advantageous to provide an electrical short circuit between such an electrode 601 located over the epileptic focus 630 and the metal case of the control module 620 which acts as an indifferent, common or ground electrode. Also, responsive stimulation using only the electrode 601 may be sufficient to abort an epileptic seizure with no other electrode being actuated.

Figure 17:
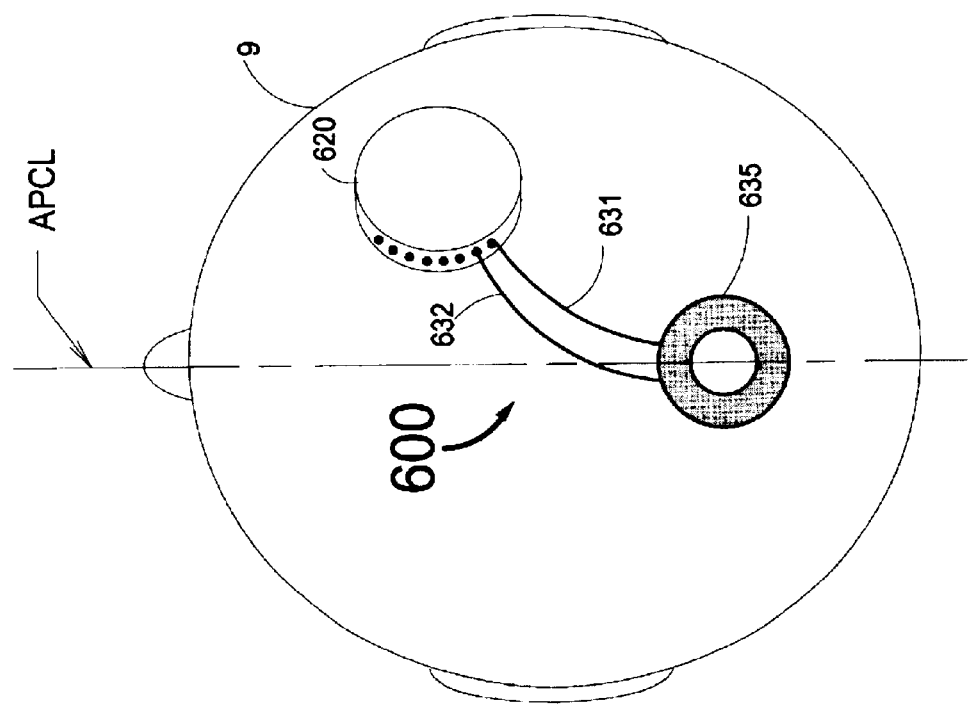
FIG. 17 is a top view of a human head showing the arrangement of an implanted input-output flat wire coil connected by wires to a control module that is implanted within the cranium.

FIG. 17 shows the location of the control module 620 connected by wires 631 and 632 to a flat wire input-output coil 635 that is placed in a posterior position on the patient's head along the APCL.

Figure 18:
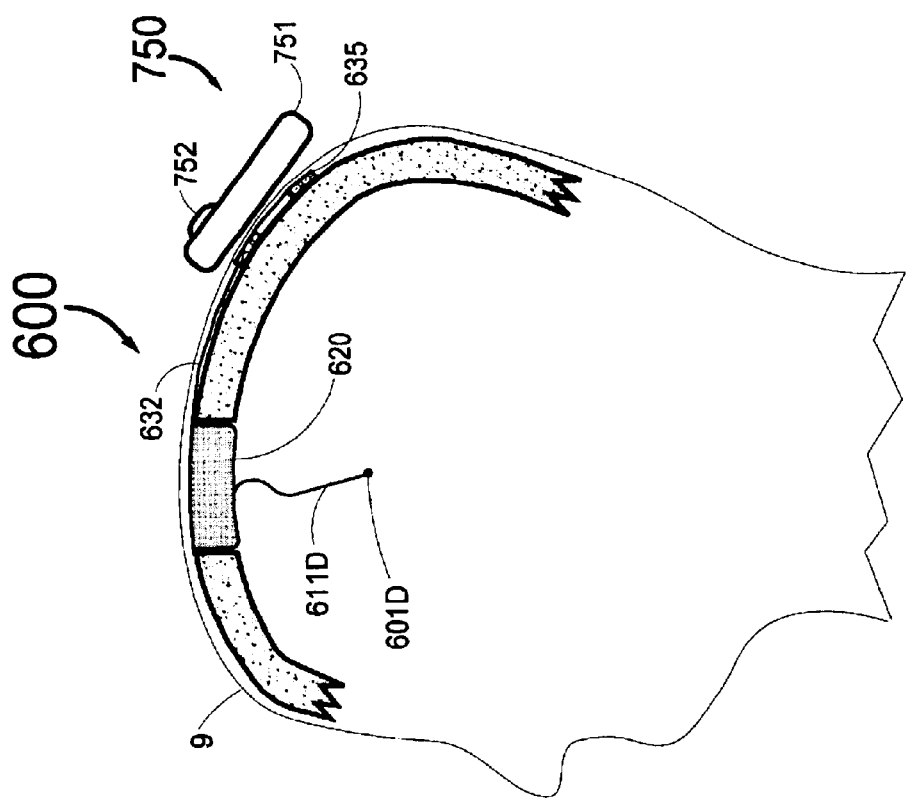
FIG. 18 is a side view of a human head showing the arrangement of the implanted input-output flat wire coil, as it would be used with a patient's initiating device to trigger some operation of the implanted system.

FIG. 18 shows a cross section of the patient's cranium along the APCL showing the cross section of flat wire coil 635 and also shows a patient initiating device 750 having a case 751 and an initiating button 752.

Figure 19:
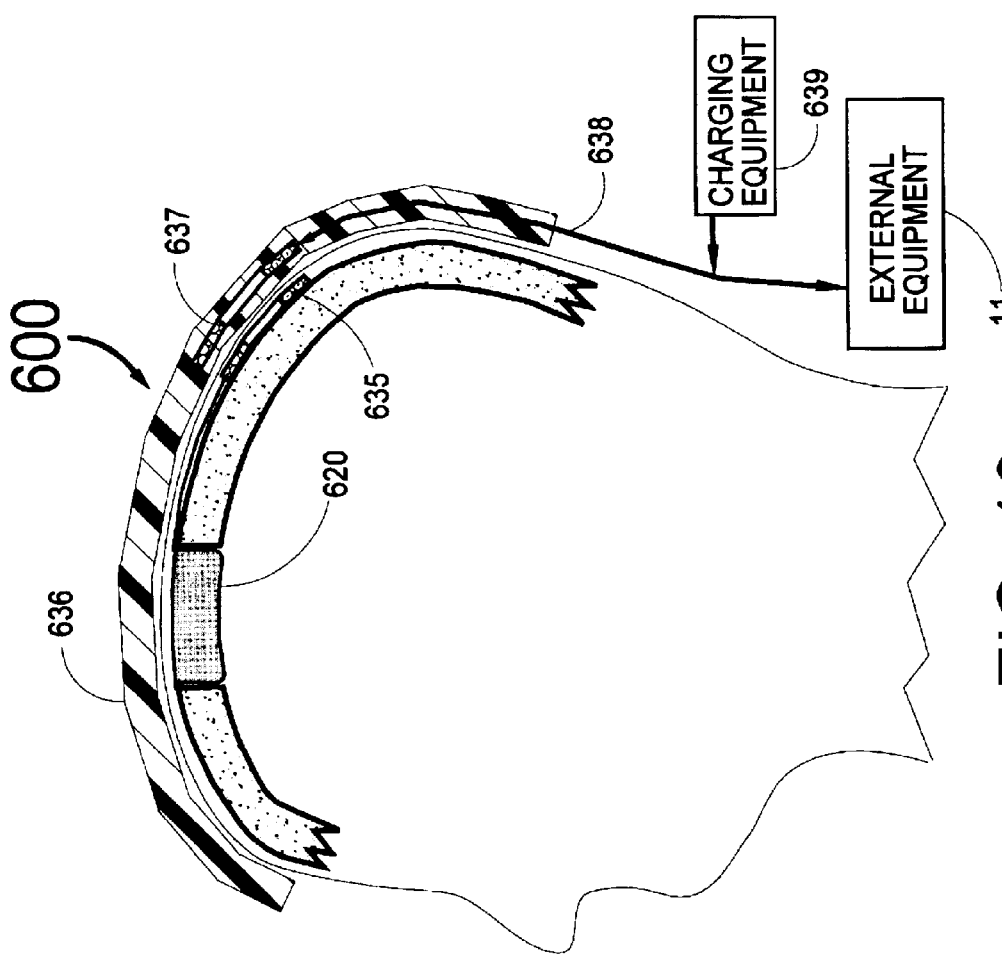
FIG. 19 is a side view of a human head showing the arrangement of the implanted input-output coil, as it would be used with a cap and with the physician's external equipment to perform some interaction with the implanted system.

FIG. 19 shows a cross section of the patient's cranium along the APCL again showing the cross section of the flat wire coil 635 and also the cross section of a cap 636 that includes a flat wire input-output communication coil 637. The flat wire coils 635 and 637 can act as emitting and receiving devices to provide two-way communication between the control module 620 and the external equipment 11.

The flat wire coil 635 serves several important functions for the operation of the implanted system 10. A first use is as the means to communicate by magnetic induction between the external equipment 11 and the implanted system 600. By "magnetic induction" is meant that an alternating magnetic field generated by (for example) the coil 638 generates an electrical current in the coil 635. Such an alternating magnetic field can also be modulated to provide the wireless two-way communication link 72 of FIG. 2. The external equipment 11 via the communication coil 637 can be used to read out telemetry stored in the control module 620 or reprogram the control module 620 with new software or operational parameters. Another use of the flat coil 635 is to allow the patient's initiating device 750 to cause a specific action to occur within the implanted system 10. For example, the device 750 can be used to trigger a response from the implanted system 600 that would be initiated by the patient when he or she feels that some neurological event was about to occur. For example, when the aura of a seizure is felt or some visual manifestation of a migraine headache, the patient would place the device 750 over the site of the implanted control module and then press the actuate button 752. The device 750 might have several buttons to initiate different responses from the implanted system 600. One response that the patient may wish to have accomplished is to hold in memory the prior several minutes of recorded EEG data if the patient feels that data may be important to an understanding of his neurological condition. Furthermore, the pressing of different buttons could be used to initiate some different response from the implanted system 600. Specifically, by pressing on the button 752, a coil within the patient's initiating device 750 can communicate by magnetic induction with the flat coil 635 to carry out a specific action such as: (1) hold data stored in the FIFOs to be read out at a later time, (2) provide a pre-programmed response to stop a neurological event, (3) turn off the implanted system, and (4) initiate any other action requested by the patient that has been pre-programmed by the physician. Another use for the flat coil 635, as shown in FIG. 19, is to connect the communication coil 637 via the wire 638 to the charging equipment 639 as required to recharge a rechargeable battery that would be located in the control module 620. The external equipment 11 could also provide electrical power to the control module 620 during readout of telemetry or during reading in of new operational parameters. Powering the control module 620 from an external source during such times of high power drains could extend the lifetime of a primary (non-rechargeable) battery located in the control module 620.

Although FIG. 17 shows the flat coil 635 located remotely from the control module 620, such a coil could also be placed on the surface of or interior to the control module 620. Remote placement has the advantage that the high frequency and intense alternating magnetic field required for communication or recharging would not be placed onto the electronics portion of the control module 620 thus avoiding interference with the operation of the system 600. The coupling by magnetic induction of the coil 635 with either the device 750 or the communication coil 637 can provide the wireless communication link 72 of FIG. 2. It is envisioned that any of the two-way communication capabilities described herein could be implemented via the electromagnetic induction structures as shown in FIGS. 17, 18, and 19, or via the radio frequency (RF) components shown in FIG. 11.

Figure 20:
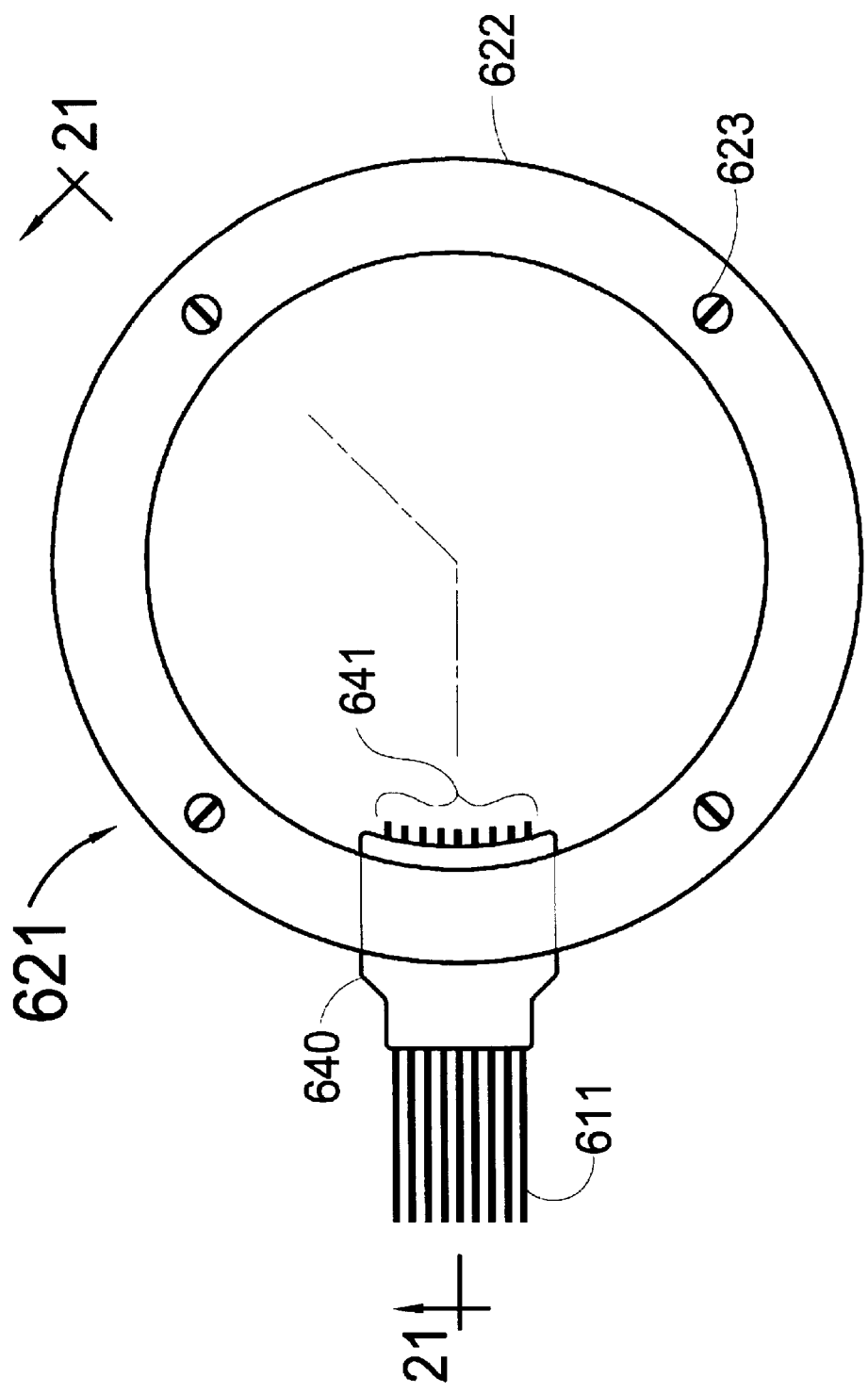
FIG. 20 is a top view of the shell of the control module.
Figure 21:
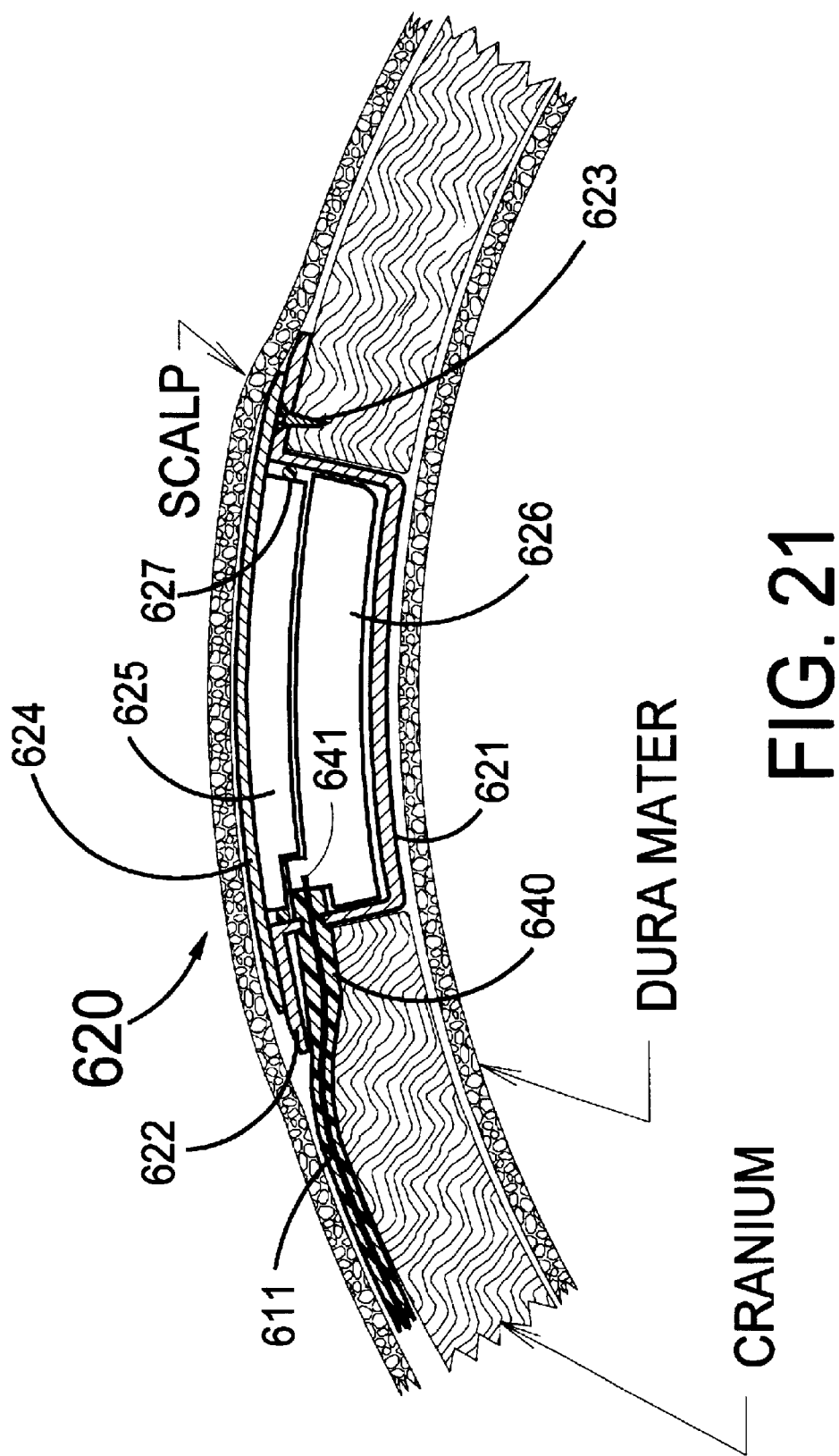
FIG. 21 is a cross section of the cranium showing a control module placed essentially within the cranium within a space where cranium bone has been removed. The cross section of the shell in FIG. 21 is taken along the section plane 21—21 of FIG. 20.

FIG. 20 is a top view of a thin-walled metal shell 621 that acts as a base for the control module 620. FIG. 21 is a cross section of the control module 620 and also shows the cross section of the shell 621 as indicated by the section 21—21 in FIG. 20. FIGS. 20 and 21 show that the shell 621 has a flange 622 and four holes through which are inserted bone screws 623 that attach the shell 621 to the bony structure of the cranium. Also shown in FIG. 20 and 21 are input wires (of which only wire 611 is indicated) that enter the insulating strain relief structure 640. On the interior of the shell 621 are male connecting pins 641 which are designed to mate with a female receptacle that forms part of the electronics module 626 that is shown in FIG. 21. The electronics module 626 contains most if not all of the electronic circuitry that is contained within the control module 620. Also shown in FIG. 21 is the battery 625, which has a top plate 624 that extends over the flange 622 of the shell 621. An O-ring 627 is used to provide a fluid seal to prevent body fluids from entering the control module 620. A silicone rubber adhesive or one or more small metal screws could be used to join the top plate 624 to the flange 622 of the shell 621. The shell 621, battery 625, and electronics module 626 constitute the three major parts of the control module 620.

The control module 620 is designed for easy implantation within a space in the cranium where the bone has been removed. The thickness of the cranium at the site of the implantation would be approximately 10 mm. Therefore, the thickness of the control module 620 would be approximately the same 10 mm with a diameter of approximately 40 mm. To implant the control module 620, the hair would be shaved over the implantation site, an incision would be made in the scalp, and the bone would be removed to make room for the control module 620. In a similar manner, holes such as H1–H4 inclusive would be made in the cranium for the pass-through of wires connecting to the brain electrodes.

Although FIG. 21 shows the electronics module 626 located beneath the battery 625, it also envisioned that those positions could be reversed if such positioning offered a more advantageous construction. In either case, either the battery 625 or the electronics module 626 could be readily replaced through a simple incision in the scalp over the site of the implanted control module 620 after the hair has been removed from the incision site.

Figure 22:
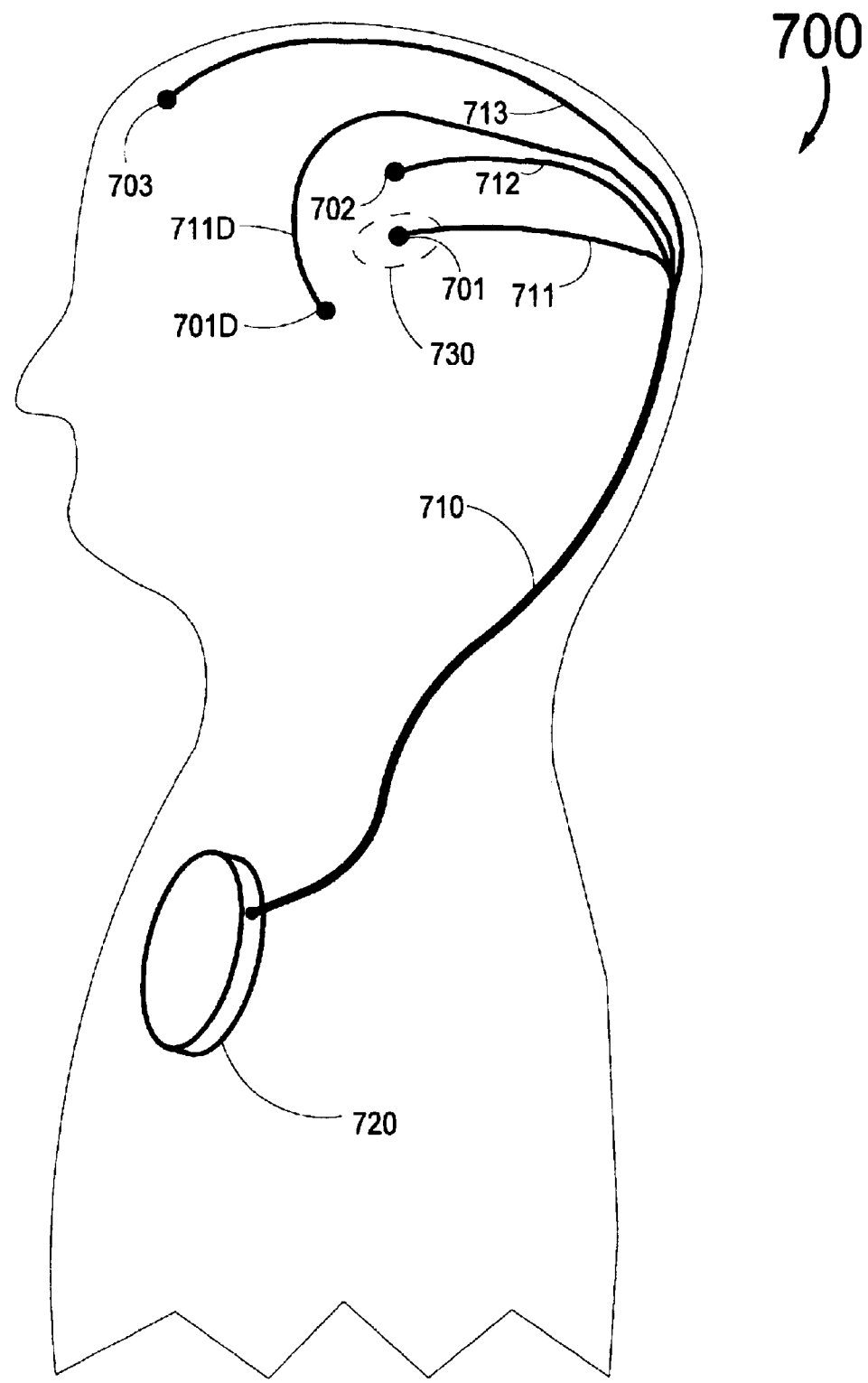
FIG. 22 is a side view of the human head and torso showing an alternative embodiment of the present invention using a control module implanted within the chest.

FIG. 22 illustrates an alternative embodiment of the invention in which the system 700 for the treatment of neurological disorders utilizes a control module 720 that is located in the patient's chest. The system 700 uses epidural electrodes 701, 702 and 703 and a deep electrode 701D; the electrodes being joined by connecting wires 711, 712, 713 and 711D, respectively, through a wire cable 710 to the control module 720. The electrode 701 is shown placed at an epileptic focus 730. This system can be used in exactly the same manner as previously described for the system 10 that had a control module 20 that was placed within the cranium.

Figure 23:
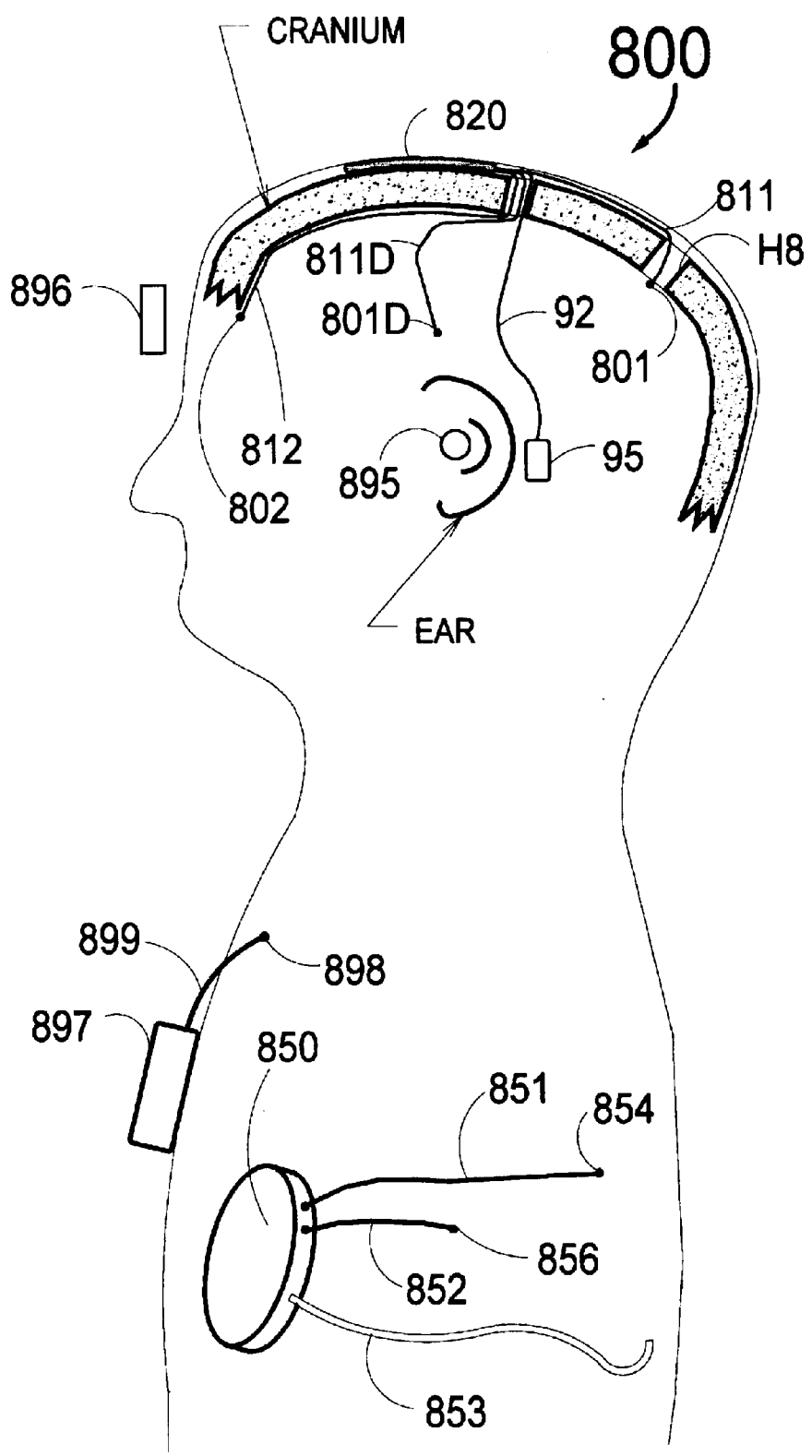
FIG. 23 is a side view of the human head and torso showing an alternative embodiment of the present invention using a control module implanted between the scalp and the cranium, a remote sensor/actuator device located within the chest, and external devices for applying acoustic, visual, or other sensory input to the patient.

FIG. 23 illustrates another embodiment of the invention that utilizes a control module placed between the patient's scalp and cranium and a remotely located implantable sensor/actuator device 850 located within the patient's body but not in the patient's head. The system 800 could operate in one of two modes. In the first mode, the sensor/actuator device 850 would operate as a sensor for sensing some physiological condition such as an elevated blood pressure or an electrical signal from a nerve or muscle indicating the presence of pain. The active electrode 854 is connected by the wire 851 to the sensor/actuator device 850 using the metal case of the sensor/actuator device 850 as an indifferent electrode. An electrical signal in the frequency range 1 to 500 kHz emitted from the electrode 854 could be used to communicate with the control module 820, thus providing a signaling means to the control module 820 from the remote sensor/actuator device 850. Of course, such signaling means can also be provided from the control module 820 to the sensor/actuator device 850. The electrical signal from the sensor/actuator device 850 would be detected between the active electrode 801 and an indifferent electrode that could be the metal case of control module 820 or it could be a separate electrode. The active electrode 801 is connected to the control module 820 by the connecting wire 811. It should be noted that in FIG. 23, the electrode 801 is placed epidurally at the bottom of the hole H8. This can be a comparatively simple way to place an epidural electrode.

Having received a signal from the sensor/actuator device 850 acting as a sensor, the control module 820 would send a signal via the wire 812 to electrode 802 to act on that portion of the brain that would result in a treatment of the physiological condition that caused the sensor/actuator device 850 to communicate with the control module 820. Thus, for example, if the electrode 854 detects a pain signal from a nerve in the back, the electrode 802 could be used to turn off a certain region of the brain so that the patient would not perceive that pain.

A second mode of operation for the system 800 would be when the intracranial portion of the system 800 is used for sensing an adverse physiological condition, and the sensor/actuator device 850 is used as an actuator to carry out some treatment at a remote location to ameliorate that adverse physiological condition. In this mode, the electrode 802 would sense the adverse condition and send an alternating electrical signal out from electrode 801 to carry out some treatment at a remote location within the body. The electrode 854 would receive that signal and could cause the sensor/actuator device 850 to carry out a pre-programmed treatment. For example, if a migraine headache is detected by the control module 820, the sensor/actuator device 850 could be instructed to release medication via the catheter 853 into the cerebrospinal fluid (the CSF) to relieve that headache. Or a Parkinson's disease tremor might be detected and the neurotransmitter epinephrine would be appropriately released into the CSF to relieve that tremor. In another example, if the patient thought about moving a certain muscle that had been made inoperative due to interrupted nerve conduction, that muscle could be activated by the electrode 856, which is connected by the wire 852 to the sensor/actuator device 850.

It should be understood that the communication signal means between the control module 820 and the sensor/actuator device 850 could be modulated by any one of several well known techniques (such as AM, FM, phase modulation, etc.) in order to carry out proportional responses based upon the sensing signal received by the electrode 802 and processed by the control module 820. It should also be understood that communication between the control module 820 and the remote sensor/actuator device 850 could be accomplished by acoustic (e.g. ultrasonic) vibrations from a buzzer at either location to a microphone at the receiving end of the transmission or by any suitable electromagnetic communication means. Of course it is also understood that a multiplicity of electrodes could be used with either the control module 820 or the sensor/actuator device 850, and that both the control module 820 and the remote sensor/actuator device 850 might together produce the response to a detected event.

It is further envisioned the signaling means between the control module 820 and the remote sensor/actuator device 850 may be in the form of either analog or digital signals.

FIG. 23 also illustrates how a buzzer 95 connected by the wires 92 to a control module 820 could be used as part of the means for stopping a neurological event such as an epileptic seizure. Since the buzzer could be located in close proximity to the ear, if it produces an acoustic output when an epileptic seizure is detected by the control module 820, that acoustic input into the brain can stop the epileptic seizure. Furthermore, a hearing aid type of acoustic output device 895 placed in the ear could have an acoustic output of a particular intensity and pitch that could turn off the seizure. The operation of either the buzzer 95 or the acoustic output device 895 would be automatic, i.e., when a seizure precursor is detected, an acoustic input signal would be applied automatically. The device 895 could be actuated by receiving a signal from the buzzer 95.

FIG. 23 also shows a visual light source 896 that could be a light emitting diode in eyeglasses worn by the patient or a special flashlight type of device. Either device could be used with a particular wavelength of light and rate of flashing on and off so as to provide a visual input that could act as a means for stopping an epileptic seizure. Although the light source 896 could be automatic if it were on a pair of eyeglasses, if a flashlight type of device is used, the visual input would be manually applied.

Also shown in FIG. 23 is a sensory actuator 897 which can apply electrical stimulation to electrodes 898 through wires 899 to the patient's skin. The sensory actuator 897 might also produce mechanical vibrations applied directly to the patient's skin.

Figure 24:
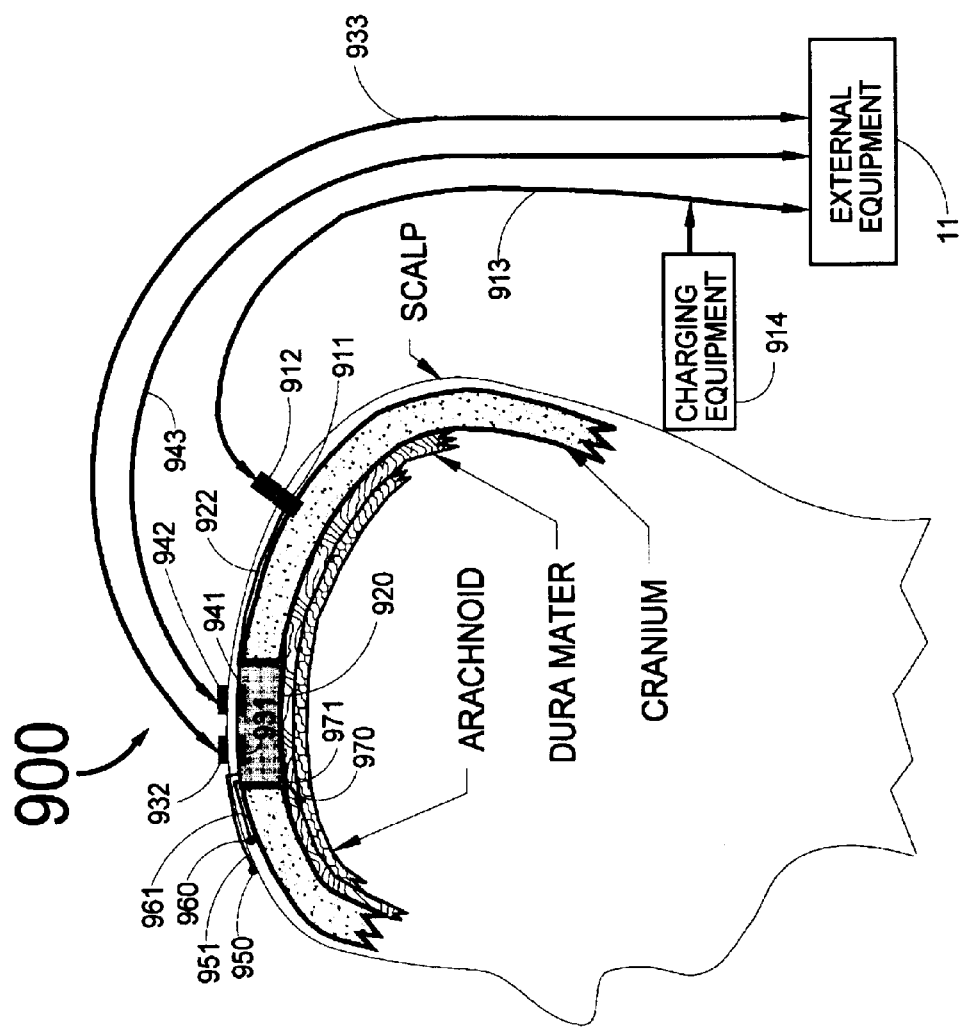
FIG. 24 is a side view of a human head showing alternative communication means between the external equipment and an implanted control module and also showing alternative locations for electrodes mounted in close proximity to the patient's brain.

FIG. 24 shows an alternative embodiment of the invention, which uses a multiple pin, pyrolytic carbon receptacle 911 placed through the patient's scalp, which receptacle provides a multiplicity of electrical connections for the control module 920. Specifically, the system 900 has a control module 920 that is electrically connected to the receptacle 911 by means of the wire cable 922. The mating plug 912 is connected by the cable 913 to provide two-way communication via electrical wires between the control module 920 and the external equipment 11. The plug 912 and cable 913 can also be used with the charging equipment 914 to recharge a rechargeable battery (not shown) located in the control module 920.

Also shown in FIG. 24 are other alternative means for providing two-way communication between the control module 920 and the external equipment 11. Specifically, FIG. 24 shows an acoustic (ultrasonic) transducer 931 mounted on the control module 920 that can communicate with the externally located transducer 932 that is in two-way communication with the external equipment 11 through the wire cable 933. In a similar manner, an infrared emitter/receiver 941 can send an infrared signal through the patient's scalp to an infrared emitter/receiver 943 that is connected by the wire cable 943 to the external equipment 11.

By any of these methods, either direct electrical connection, or acoustic or infrared two-way communication the equivalent function of element 72 in FIG. 2 can be accomplished. It has already been established that two-way communication 72 can also be accomplished by a variety of electromagnetic means including an alternating magnetic field or by radio frequency communication.

FIG. 24 also shows other locations for electrodes that are to be placed in close proximity to the brain. Specifically, FIG. 24 shows an electrode 950 mounted on the outer surface of the scalp that is connected by the cable wire 951 to the control module 920. Such an external electrode 950 could also be used with an externally placed control module (not shown). Additionally, electrodes such as the electrode 960 could be placed between the patient's scalp and cranium and would be connected by the wire cable 961 to the control module 920. Furthermore, electrodes such as the electrode 950 could be placed between the dura mater and the arachnoid and would be connected via the wire cable 971 to the control module 920.

It should be noted that any of the electrodes described herein that are in the general proximity of the brain either inside or on top of the patient's head or deep within the patient's brain can all be considered to be "brain electrodes."

Figure 25:
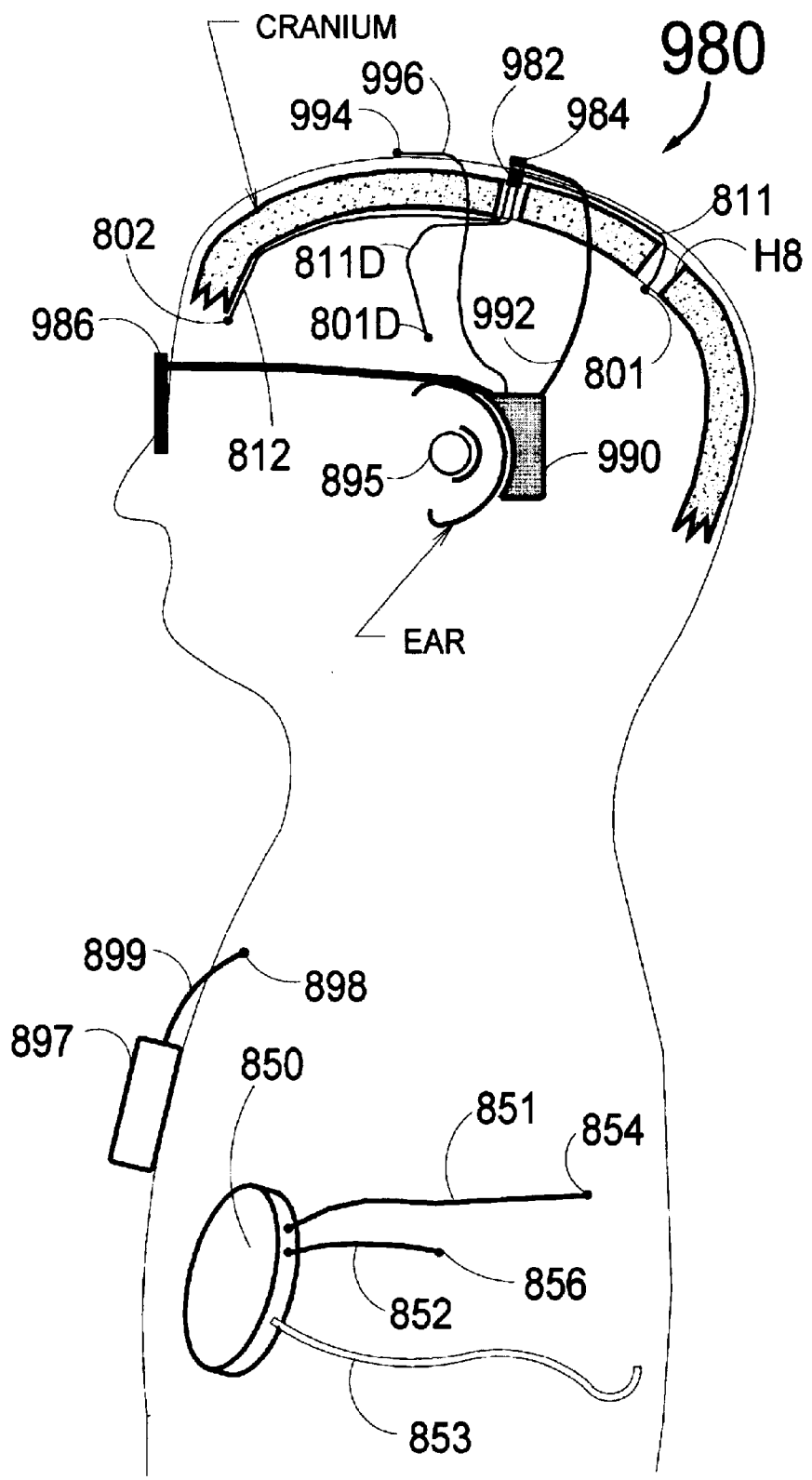
FIG. 25 is a side view of the human head and torso showing an alternative embodiment of the present invention using a control module located external to the patient's body and a remote sensor/actuator device located within the chest, and external devices for applying acoustic, visual, or other sensory input to the patient.

FIG. 25 illustrates a system 980 for the treatment of neurological disorders that uses an external control module 990 with either internal or external means for stopping a neurological event. Specifically, the scalp-mounted electrode 994 connected by the wire 996 to the control module 990 could be used to detect a neurological event. Of course one could use a multiplicity of such scalp-mounted electrodes. Once a neurological event has been detected, the control module 990 could actuate an acoustic input device 895, or a visual light input device 986 or an actuator 897 for other sensory inputs. Thus, such a system 980 envisions a control module 990 mounted external to the patient that uses external remote actuators that can provide acoustic, visual or other sensory inputs that could stop an epileptic seizure.

Furthermore, the system 980 envisions the use of the externally mounted control module 990 with electrodes mounted in close proximity to the brain or actually within the brain (i.e. "brain electrodes"). Specifically, the electrodes 801 and 802 could be mounted on the dura mater and a deep electrode 801D could be placed within the brain itself. The wires 811, 812 and 811D could be connected to receptacle 982 that is mated to the plug 984 that connects by the wire 992 to the control module 990. The electrodes 801, 802 and 801D could be used either for sensing a neurological event or for providing an electrical stimulation to stop such a neurological event.

In FIG. 25, the remote sensor/actuator device 850 can be used as part of the means for stopping a neurological event by applying an electrical stimulus to one or two vagus nerves by means of the electrodes 854 and/or 856. This could also be accomplished using the system shown in FIG. 23, i.e., with any control module 820 (or 20) that is implanted beneath the scalp. In FIG. 25 the catheter 853 can be used to apply medication as part of the means for stopping a neurological event. The sensor/actuator device 850 can be triggered to stop the neurological event by means of a signal originating from the externally mounted control module 990.

Also shown in FIG. 25 is an external remote actuator 897 which can apply electrical stimulation to electrodes 898 through wires 899 to the patient's skin. The actuator 897 might also produce mechanical vibrations applied directly to the patient's skin as another form of sensory input.

Figure 26:
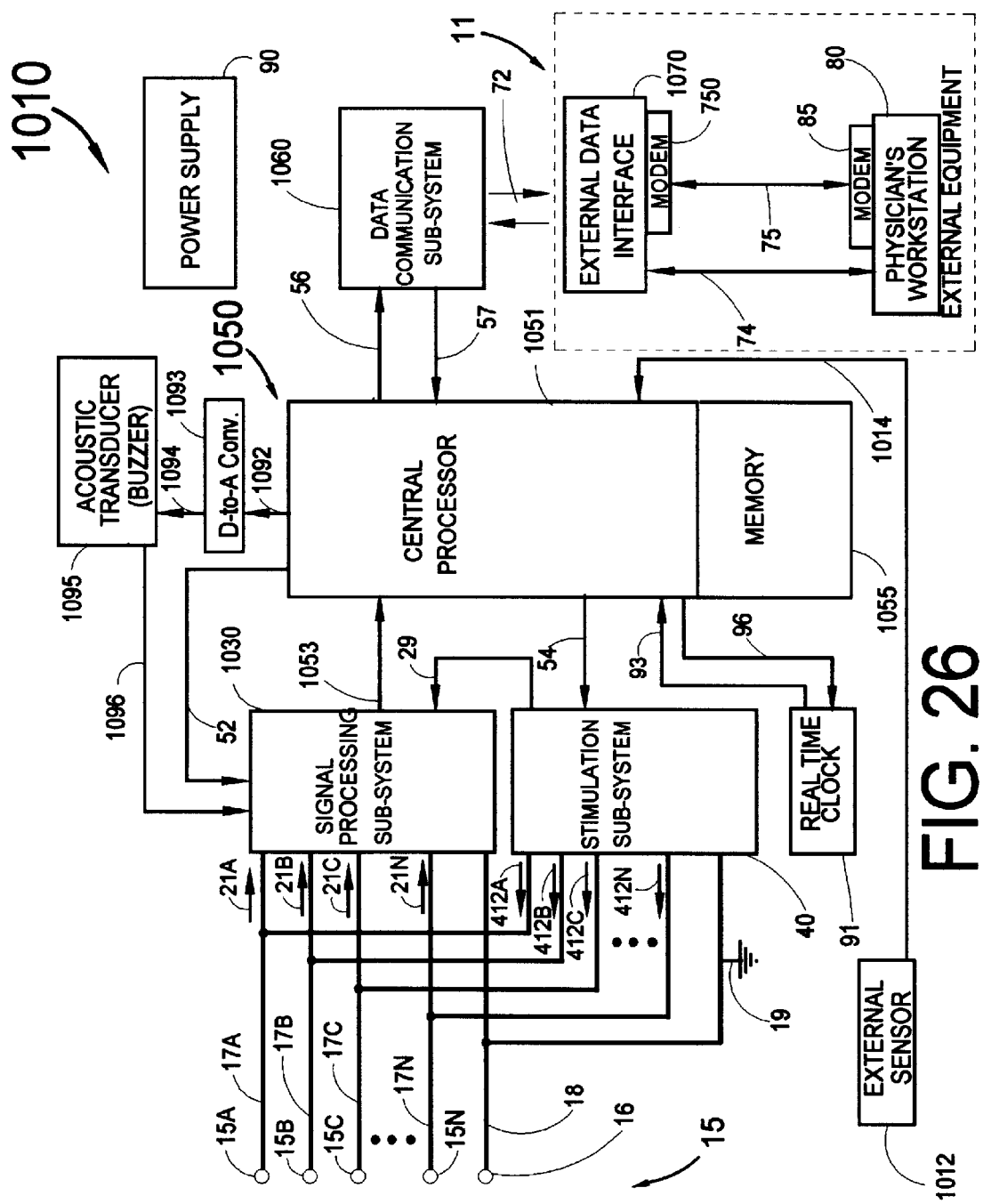
FIG. 26 is a block diagram of the implanted and external portions of an alternate embodiment of the system having enhanced patient communication capabilities.

FIG. 26 is a block diagram of the implanted and external portions of an alternate embodiment of the system 1010 having enhanced patient communication capabilities. This embodiment is similar to that of FIG. 2 with the "buzzer" 95 of FIG. 2 now called an acoustic transducer 1095 and the acoustic transducer 1095 also having connection to the event sub-system now called the signal processing sub-system 1030 that allows the acoustic transducer 1095 to act as a microphone in picking up mechanical vibrations including but not limited to human speech.

The wires 17A through 17N from the electrodes 15A through 15N, and the wire 18 from the common electrode 16, are shown connected to both the signal processing sub-system 1030 and the stimulation sub-system 40. It is also envisioned to use the case of the control module 20 of FIG. 1 as the common (or indifferent) electrode 16. The wires 17A through 17N carry EEG signals 21A through 21N from the electrodes 15A through 15N to the signal processing sub-system 1030. The electrodes 15A through 15N can be energized by the stimulation sub-system 40 via the wires 17A through 17N to electrically stimulate the patient's brain using the stimulation signals 412A through 412N respectively. Although the electrodes 15A through 15N and 16 shown here are connected to both the signal processing sub-system 1030 and the stimulation sub-system 40, it is obvious that a separate set of electrodes and associated wires could be used with each sub-system. Furthermore, it is envisioned that any one, several or all of the electrodes 15A through 15N could be electrically connected (i.e., shorted) to the electrode 16 or to each other. This would be accomplished by appropriate switching circuitry in the stimulation sub-system 40.

The signal processing sub-system 1030 receives the EEG signals 21A through 21N (referenced to system ground 19 connected to the wire 18 from the common electrode 16) and processes them to identify neurological events such as an epileptic seizure or its precursor. A central processing system 1050 with central processor 1051 and memory 1055 acts to control and coordinate all functions of the implantable system 1010. The interconnection 1052 is used to transmit programming parameters and instructions to the signal processing sub-system 1030 from the central processing system 1050. The interconnection 1053 is used to transmit signals to the central processing system 1050 identifying the detection of a neurological event by the signal processing sub-system 1030. The interconnection 1053 is also used to transmit EEG and other related data for storage in the memory 1055. In addition, the interconnection 1053 is used to transmit processed acoustic signals from the acoustic signals from the acoustic transducer 1095 that have been signal processed by the signal processing sub-system 1030.

When an event is detected by the signal processing sub-system 1030, the central processor 1051 can command the stimulation sub-system 40 via the interconnection 54 to transmit electrical signals to any one or more of the electrodes 15A through 15N via the wires 17A through 17N. It is anticipated that, if appropriate electrical signals 412A to 412N inclusive are transmitted to certain locations in or near the brain, the normal progression of an epileptic seizure can be aborted. At the same time or just before or just after the application of electrical stimulation by the stimulation sub-system 40, an electrical signal can be sent from the central processor 1051.

A power supply 90 provides power to each component of the system 1010. Power supplies for comparable implantable devices such as heart pacemakers and heart defibrillators are well known in the art of implantable electronic devices. Such a power supply typically utilizes a primary (non-rechargeable) storage battery with an associated DC-to-DC converter to obtain whatever voltages are required for the implantable system 1010.

Data stored in the memory 1055 can be retrieved by the patient's physician by a wireless communication link 72 with the data communication sub-system 60 connected to the central processing system 1050. An external data interface 1070 can be directly connected with an RS-232 type serial connection 74 to the physician's workstation 80. Alternately, the serial connection may be via modems 85 and 750 and phone line 75 from the patient's home to the physician's workstation 80. The software in the computer section of the physician's workstation 80 allows the physician to read out a history of events detected including EEG information before, during, and after the event as well as specific information relating to the detection of the event such as the time evolving energy spectrum of the patient's EEG. The workstation 80 also allows the physician to specify or alter the programmable parameters of the implantable system 1100.

The acoustic transducer 1095 (buzzer) is connected by the link 1094 to the digital-to-analog converter 1093 that is connected to the central processor 1051 via the link 1092. The acoustic transducer 1095 can be used to notify the patient that an event has occurred or that the implanted system 1010 is not functioning properly. The acoustic transducer could provide a mechanical vibration (typically an acoustic signal) that could be perceived by the patient. By placing the acoustic transducer 1095 near the ear and on the top of, below, or within a burr hole in the cranium, an acoustic signal emitted by the acoustic transducer 1095 will be detectable by the patient's ear.

It is also envisioned that the acoustic transducer 1095 could be part of the electronics module 626 shown in FIG. 21. In this embodiment the acoustic transducer 10 would be in contact with the thin-walled metal shell 621 of the control module 620 shown in FIG. 21. In this configuration, the vibration of the acoustic transducer 1095 will be heard by the patient through bone conduction with the advantage of having the acoustic transducer 1095 not be separate from the control module. This sound produced by the acoustic transducer 1095 itself can be an automatic means for stopping an epileptic seizure.

The acoustic signal delivered by the acoustic transducer 1095 can be a buzz, a tone, a sequence or combination of tones, a segment of recorded music, a synthesized or reproduced complex sound, or a segment of human speech. The speech could be either synthesized human speech or recorded and digitally encoded human speech stored in the memory of the control module or transmitted from the external equipment 11 to the control module. The acoustic transducer 1095 would typically be a small acoustic transducer such as a piezoelectric crystal or the miniature loudspeaker from a hearing aid. The speech segments could be stored in the digital memory 1055 of the system 1010 using encoding methods including but not limited to PCM, ADPCM, or LPC (or variations thereof, such as CELP, code-excited linear prediction) and played out through a digital-to-analog converter 1093 to the buzzer 1095. Although not shown in FIG. 26, an amplifier may be used to increase the signal strength on the link 1094 if the output of the digital-to-analog converter 1093 is insufficient to drive the buzzer 1095.

Similarly, a complex sound can be generated as an electrical signal by known analog or digital sound synthesis methods or by known analog or digital sound reproduction methods (such as PCM- or ADPCM-encoded waveforms stored in digital memory and played through a digital-to-analog converter).

Speech synthesis integrated circuits that can convert text into human speech are well known. Such a speech synthesis chip could be inserted between the processor 1051 and the digital-to-analog converter 1093. This would allow the voice announcements to be stored as text strings instead of encoded voice recordings reducing the amount of digital memory required.

As set forth above, the buzzer 1095 or acoustic transducer of the present invention is designed to provide audible information via vibrations to a person with an ordinary (or functional) level of hearing. Buzzes, tones, combinations or sequences of tones, complex sounds, or segments of reproduced or synthesized human speech are used by the invention to provide information to the patient regarding, in various embodiments, the state or function of the device or conditions identified by the device. These sounds are transmitted to the patient's ears, preferably via bone conduction through the cranium, but possibly simply through the air. Furthermore, a device according to the invention would generate specific sounds, as set forth above, and generally would not amplify external ambient sound for transmittal to and electrical stimulation of the middle or inner ear. A device according to the invention is not adapted to provide hearing assistance; it is designed to provide information to the patient.

The acoustic transducer 1095 can also act as a microphone to convert mechanical vibration into electrical signals that can be processed by the signal processing sub-system 1030. Most signal processing chips can be programmed to recognize spoken words as well as other electrical signals. Thus the signal processing sub-system 1030 might be programmed to detect neurological events by processing EEG signals and simultaneously be programmed to recognize spoken commands picked up by the acoustic transducer 1095. Alternately, a sequence of tapping on the head near the control module could be used to command the system 1010 or to turn on the speech detection program. For example, detecting two sets of 5 taps with less than 10 seconds between the sets could is a signal that would be unlikely to be accidentally produced by natural events. Such detection is straightforward for the event recording and processing system 360 with programmable components like the event density counter 371 shown in FIG. 7. With tap detection using 1 tap for yes and 2 taps for no, in response to speech prompts delivered by the acoustic transducer 1095, a means for patient communication with an implanted device can be accomplished without the need for any external equipment. This would also eliminate the need for an external magnet such as is used with heart pacemakers and implantable defibrillators to change system modes of the implantable device.

Although a single acoustic transducer 1095 is shown in FIG. 26, separate microphone and loudspeaker transducers could be used instead.

The ability to communicate with the patient from an implantable device has applications beyond notification of detected neurological events. Such communication can be reminders to the patient to take medications, warnings that the device battery is low and needs recharging or replacements or just a daily notification that the system is functioning properly. If the system 1010 is acting only as a neurological event detector without stimulation, the announcement could tell the patient to take medication, sit down, or stop activities because a seizure is about to begin.

The external data interface 1070 can be a personal computer, a PDA such as a 3Com Palm Pilot or handheld PC running Microsoft Windows CE. It could also be a modified wireless phone that might have the modem for external data transmission built in allowing contact between the patient and doctor from any location.

It is also envisioned that the system 1010 could work cooperatively with the external data interface 1070 in the following ways. A simple, tone, buzz or announcement played through the acoustic transducer 1095 that will prompt the patient to get within a specific distance of the external data interface 1070. Once within this distance the implanted system 1010 can communicate with the external data interface 1070 to facilitate one or more of the following tasks.
1. The external data interface 1070 could provide text or speech instructions to the patient for taking medications related to the condition detected by the system 1010.
2. Remind the patient that it is time to take medication.
3. The external data interface 1070 could instruct the patient to schedule an appointment with the physician.
4. Answer an incoming phone call.
5. Place a phone call to a number listed on the external data processor display. This is a function similar to a pager.
6. The external data interface 1070 could automatically call for an ambulance or paramedic if the condition was severe.
7. The external data interface 1070 could retrieve data from the memory 1055 and transmit it on to the physician's workstation 80.

The present invention of particular importance associated with detection of a precursor. With the ability to detect the precursor that is a first neurological event of a second neurological event that would have clinical manifestations, an alert to take medication could be extremely effective in averting a seizure. Techniques for the prediction of epileptic seizures have been widely published by Osorio and others and indicate that it can be possible to detect the precursor electrical signal predictive of the onset of a seizure many minutes before the clinical symptoms appear.

Only the acoustic transducer 1095 need be positioned so that mechanical vibration produced would be detectable by the patient's ears. The remainder of the system might be implanted elsewhere in the body like the control module 720 of FIG. 22. The acoustic transducer 1095 could also be part of an external device such as the control module 99 of FIG. 25 that sits behind the patient's ear.

The system 1010 has a wireless external communication link 72 that could allow external equipment to initiate the acoustic signals played to the patient by the acoustic transducer 1095. Such signals could include instructions for downloading stored EEG data stored in the memory 1055 through the modem 750 to the Physician's workstation 80.

Other signals of interest for the present invention could be the ringing or voice signals received by a telephone or an alarm generated by the external equipment 11.

A real time clock 91 is used for timing and synchronizing various portions of the implanted system 10 and also to enable the system to provide the exact date and time corresponding to each neurological event that is detected by the implantable system 1010 and recorded in memory. The interconnection 96 is used to send data from the central processor 1051 to the real time clock 91 in order to set the correct date and time in the clock 91. The real time clock 91 is useful if a daily message such as "System OK" is played at noon each day to the patient through the acoustic transducer 1095.

FIG. 26 also shows an implantable external sensor 1012 with link 1014 to the central processor 1051. Examples of implantable external sensors envisioned are:

1. A pressure sensor for use in sensing blood pressure, intra-cranial pressure or pressure at any other desirable location within the human body. Such a system with a blood pressure sensor could prompt the patient to take medication to reduce their high blood pressure. Also, when used in conjunction with a drug infusion device the system 910 of FIG. 14 with infusion pump 91 and catheter 92 or the remote module 850 of FIG. 23 having drug delivery catheter 853, the system could automatically infuse medication to counteract the abnormal pressure detected by the pressure sensor. Such a pressure sensor could be made from a Piezo-electric crystal.
2. A temperature sensor.
3. A blood gas sensor. This could be used for underwater divers to sense nitrogen in the blood and warn of potential decompression sickness or, when decompressing, when it is save to stop.
4. A chemical sensor that can provide data on the concentration of specific chemical compounds within some part of the human body. For example, Minimed Technologies has developed an implantable glucose sensor. A glucose imbalance in a diabetic could prompt the present invention to play the appropriate message to the patient. It is also possible that specific electrical stimulation within the brain or elsewhere within the body could be used to induce the body to increase the production of the chemical.
5. A heart rate sensor.

The external sensor 1012 would generate sensor electrical signals that it would transmit through the link 1014 to the electronic circuitry of the system 1010 and specifically to the central processor 1051. It is envisioned that the system 1010 could emit acoustic signals in response to changes in the electrical signals sent from the sensor 1012 to the central processor 1051.

Additional objects and advantages of the present invention will become apparent to those skilled in the art to which this invention relates from the subsequent description of the preferred embodiments and the appended claims, taken in conjunction with the accompanying drawings.

What is claimed is:
1. A system for acoustic communication with a human patient having a body including a head, comprising:
   a control module implanted within the patient's body, wherein the control module comprises electronic circuitry capable of generating an electrical signal;
   an acoustic transducer implanted within the patient's head, wherein the acoustic transducer is capable of emitting an acoustic signal audible to the patient, the acoustic signal being emitted in response to the electrical signal; and
   an electrical connection between the control module and the buzzer.
2. A system for acoustic communication with a human patient having a body including a head, comprising:
   a control module implanted within the patient's body, wherein the control module comprises electronic circuitry capable of generating an electrical signal;
   a buzzer implanted within the patient's head, wherein the buzzer is capable of emitting an acoustic signal audible to the patient, the acoustic signal being emitted in response to the electrical signal; and
   an electrical connection between the control module and the buzzer.
3. The system of claim 2, wherein the patient's head has a scalp and the buzzer is implanted beneath the scalp.

4. The system of claim 2, wherein the patient's head has a cranium and the buzzer is implanted intracranially.

5. The system of claim 2, wherein the patient's body has skin, and the control module is implanted beneath the skin.

6. The system of claim 2, wherein the control module further comprises a housing having an outer surface, and wherein the buzzer is mechanically coupled to the housing.

7. The system of claim 6, wherein the patient's head has a cranium and the control module is implanted intracranially.

8. The system of claim 2, wherein the patient's head has an ear and the buzzer is adapted to transmit the acoustic signal via bone conduction to the ear.

9. The system of claim 2, wherein the acoustic signal comprises a buzzing sound, a tone, a sequence of tones, a combination of tones, a complex sound, or a segment of human speech.

10. The system of claim 2, wherein the electronic circuitry is adapted to generate the electrical signal to emit the acoustic signal in response to detection of a neurological event.

11. The system of claim 2, wherein the electronic circuitry is adapted to generate the electrical signal at a pre-specified time.

12. The system of claim 2, wherein the acoustic signal is representative of an instruction to the patient.

13. The system of claim 2, wherein the acoustic signal is representative of information to be communicated to the patient.

14. The system of claim 2, further comprising an external interface adapted to be placed near to the patient, for providing two-way communication between the control module and an external apparatus.

15. The system of claim 14, wherein the external interface includes the external apparatus.

16. The system of claim 14, wherein the external interface is adapted to transmit a data signal from the control module to the external apparatus and a command signal from the external apparatus to the control module.

17. The system of claim 14, wherein the external apparatus comprises a personal computer, a portable computer, or a PDA.

18. The system of claim 14, wherein the external apparatus is adapted to provide instructions or information to the patient in response to data received from the control module.

19. The system of claim 18, wherein the acoustic signal is representative of an instruction to the patient to employ the external interface to transmit data between the control module and the external apparatus.

20. The system of claim 18, wherein the acoustic signal is representative of an instruction to the patient to receive instructions or information from the external apparatus.

21. The system of claim 14, wherein the external data interface is adapted to communicate via a telephone line.

22. The system of claim 14, wherein the external data interface is adapted to communicate via the Internet.

23. The system of claim 2, wherein the buzzer comprises a piezoelectric crystal adapted to emit the acoustic signal in response to the electrical signal.

24. The system of claim 2, wherein the buzzer comprises a mechanical vibrator or an electrical scalp stimulator.

25. The system of claim 2, wherein the buzzer comprises an acoustic transducer.

26. The system of claim 25, wherein the acoustic transducer is adapted to emit an electrical output in response to a vibration.

27. The system of claim 26, wherein the electronic circuitry is adapted to process the electrical output received from the acoustic transducer.

28. The system of claim 27, wherein the electronic circuitry is further adapted to detect and identify a spoken word received by the acoustic transducer.

29. The system of claim 27, wherein the electronic circuitry is further adapted to detect and identify a sequence of taps received by the acoustic transducer, wherein the sequence of taps represents a command.

30. The system of claim 2, further comprising a brain electrode electrically coupled to the electronic circuitry, wherein the brain electrode is adapted to detect electrical activity representative of a neurological event and transmit an activity signal representative of the electrical activity to the electronic circuitry.

31. The system of claim 30, wherein the electrical activity comprises an EEG signal.

32. The system of claim 30, wherein the electronic circuitry is further adapted to detect the neurological event and generate the electrical signal in response thereto.

33. The system of claim 30, wherein the neurological event is an epileptic seizure, a precursor to an epileptic seizure, a Parkinson's tremor, a precursor to a Parkinson's tremor, a migraine headache, a precursor to a migraine headache, or depression.

34. The system of claim 2, further comprising a sensor electrically coupled to the electronic circuitry, wherein the sensor is adapted to detect a condition within the body and transmit information representative of the condition to the electronic circuitry.

35. The system of claim 34, wherein the sensor is adapted to detect blood pressure, intracranial pressure, temperature, the concentration of a chemical compound, or heart rate.

* * * * *